United States Patent
Watanabe et al.

(10) Patent No.: US 7,892,821 B2
(45) Date of Patent: Feb. 22, 2011

(54) CULTURE CHAMBER, CULTURE APPARATUS AND LIQUID SUPPLYING METHOD FOR CELL OR TISSUE CULTIVATION

(75) Inventors: Setsuo Watanabe, Fuji (JP); Yoshinobu Masuda, Fuji (JP); Shuji Inagaki, Fuji (JP)

(73) Assignee: Takagi Industrial Co., Ltd., Fuji-shi (JP)

( * ) Notice: Subject to any disclaimer, the term of this patent is extended or adjusted under 35 U.S.C. 154(b) by 975 days.

(21) Appl. No.: 11/307,692

(22) Filed: Feb. 17, 2006

(65) Prior Publication Data

US 2007/0020750 A1    Jan. 25, 2007

(30) Foreign Application Priority Data

Jul. 19, 2005    (JP) .............................. 2005-208752

(51) Int. Cl.
C12M 1/00 (2006.01)
C12M 3/00 (2006.01)
C12M 1/22 (2006.01)
B01L 3/00 (2006.01)

(52) U.S. Cl. ................... 435/305.1; 435/93; 435/284.1; 435/289.1; 435/286.5; 435/288.1; 435/299.1; 435/304.1; 435/305.4; 422/99; 422/102

(58) Field of Classification Search .................. 435/93, 435/284.1, 289.1, 286.5, 288.1, 299.1, 304.1, 435/305.1, 305.4; 422/99, 102
See application file for complete search history.

(56) References Cited

U.S. PATENT DOCUMENTS 4,908,319 A * 3/1990 Smyczek et al. ......... 435/305.4

(Continued)

FOREIGN PATENT DOCUMENTS

EP    1 382 670 A1    1/2004

(Continued)

OTHER PUBLICATIONS

John G. Aunins et al., "Fluid Mechanics, Cell Distribution, and Environment in CellCube Bioreactors," Biotechnol. Prog. 2003, 19, 2-8.

(Continued)

*Primary Examiner*—William H Beisner
*Assistant Examiner*—Nathan A Bowers
(74) *Attorney, Agent, or Firm*—Connolly Bove Lodge & Hutz LLP

(57) ABSTRACT

A culture chamber which cultivates a culture object by using a culture liquid has a culture space part which houses the culture object together with the culture liquid, an introducing part (an introducing port) which introduces the culture liquid into the culture space part, a discharging part (a discharging port) which discharges the culture liquid from the culture space part, and a flow arrangement part (a vertical wall, a small space part). The flow arrangement part is formed in a side of the introducing part of the culture space part, and causes a liquid flow, which reaches to the discharging part, to the culture liquid introduced into the culture space part from the introducing part by diffusing from inner wall surfaces of the culture space part toward a direction which intersects a virtual line connecting the introducing part and the discharging part.

16 Claims, 23 Drawing Sheets

U.S. PATENT DOCUMENTS

| | | | | |
|---|---|---|---|---|
| 5,744,366 | A | * | 4/1998 | Kricka et al. ................ 436/63 |
| 5,843,766 | A | * | 12/1998 | Applegate et al. ........ 435/284.1 |
| 5,989,913 | A | | 11/1999 | Anderson et al. |
| 2004/0235153 | A1 | | 11/2004 | Takagi et al. |
| 2007/0264704 | A1 | * | 11/2007 | Van Toever ................ 435/262 |

FOREIGN PATENT DOCUMENTS

| | | |
|---|---|---|
| EP | 1 428 869 | 6/2004 |
| JP | 63 233779 A | 9/1988 |
| JP | 2003-61642 | 3/2003 |
| JP | 2004-016194 | 1/2004 |
| JP | 2004-147555 | 5/2004 |
| JP | 3572341 | 7/2004 |
| JP | 2005-218368 | 8/2005 |
| WO | WO-9015859 A | 12/1990 |

OTHER PUBLICATIONS

Setsuo Watanabe et al., "Hydrostatic Pressure/Perfusion Culture System Designed and Validated for Engineering Tissue," J. Biosci. Bioeng., vol. 100, No. 1, 105-111, 2005.

Japanese Office Action issued in corresponding Japanese Patent Application No. 2005-208752 dated Sep. 28, 2010.

Korean Office Action issued in corresponding Korean Patent Application No. 10-2006-12511 dated Aug. 30, 2007.

* cited by examiner

CULTURE CHAMBER, CULTURE APPARATUS AND LIQUID SUPPLYING METHOD FOR CELL OR TISSUE CULTIVATION

CROSS REFERENCE TO RELATED APPLICATIONS

This application is based upon and claims the benefit of priority from the prior Japanese Patent Application No. 2005-208752, filed on Jul. 19, 2005, the entire contents of which are incorporated herein by reference.

BACKGROUND OF THE INVENTION

1. Field of the Invention

The present invention relates to a culture chamber used for the cultivation of cells or tissues of a human being or an animal. In particular, it relates to a culture chamber using a culture liquid, a culture apparatus using the culture chamber, and a liquid supplying method using the culture chamber.

2. Description of the Related Art

In the cultivation of cells or tissues of a human being or an animal, a culture liquid is used, and a vessel, such as a Petri dish, which houses the culture liquid and the cells or tissues, is used. By using them, a technology which makes the cells or tissues glow in the culture liquid within the vessel has been known. The culture liquid is a culture medium for the cells or tissues, and also performs a function as a transmission medium of nutrient and air such as oxygen. In the process of cultivation, nutrient, oxygen and so on are absorbed into the cells or tissues from the culture liquid. Because of this, in order to maintain the cells or tissues in a fresh condition by the supply of nutrient necessary for the cells or tissues, the removal of wastes, and so on, an exchange of the culture liquid is indispensable. For this exchange of the culture liquid, for example, a system which makes the culture liquid circulate from a source of the culture liquid to the vessel housing the cells or tissues through a circuit is used. In order to prevent the contamination of the culture liquid and a culture object due to unwanted bacteria, an airtight vessel and a closed system circuit are used in a system like this, for example.

In connection with such an exchange of a culture liquid and so on, there are a cell culture apparatus (The Japanese Laid Open Publication No. 2004-016194: a patent document 1) which performs the culture of cells while carrying out an exchange of a culture medium in a culturing container under a state separated from an outer environment, a cell and tissue culturing device (The Japanese Laid Open Publication No. 2003-061642: a patent document 2) which supplies a culture liquid to a chamber provided in a closed system circuit, a cell culture apparatus (The Japanese Laid Open Publication No. 2004-147555: a patent document 3) which makes a culture liquid and oxygen perfuse, and so on.

By the way, in the technology (the patent document 1) performing the exchange of a culture medium by sucking in cells, which are separated from an outer environment by a culture vessel, with a pipette nozzle and removing it to another culture vessel, or by injecting a new culture medium after sucking in a culture medium within a culture vessel to remove it, it is feared that unnecessary stress is applied to the cells under cultivation. Further, it is feared that the cells are lost due to the exchange of a culture medium, and so on. For example, as shown in FIG. 22, if a culture liquid 202 is injected to a culture object 204, which is housed in a Petri dish 200 together with the culture liquid 202, by a pipette nozzle 206, the culture liquid 202 which is injected makes a compressive force (a) and a shearing force (b) act on the culture object 204. Because of this, it is feared that these make stress against the culture object 204 and also make an outflow (c) of the cells from the culture object 204.

Further, in the cultivation (the patent document 2) using a closed system circuit, it is possible to perform the circulation of a culture liquid by the drive of a piston. However, it is feared that this circulation of the culture liquid gives excessive physical stimulation to a culture object, and that the physical stimulation changes it into cells or tissues having a character not able to forecast. For example, as shown in FIG. 23, in case in which a culture liquid 202 is injected into a culture chamber 208, which is provided in a closed circuit, through a tube path 210, a jet flow is generated in the vicinity of an entrance of the culture chamber 208, and the culture liquid 202 in the culture chamber 208 joins in the vicinity of its exit and increases its flow velocity. Because of this, it is feared that the cells and an extracellular matrix 212 receive a compressive force due to the jet flow in the vicinity of the entrance, and that the cells and an extracellular matrix 212 receive a high-speed flow to flow out in the vicinity of the exit. Further, it is also feared that, depending on stress given to the cells or tissues, these are changed into cells or tissues which have a character out of a purpose.

Like this, since the exchange of a culture liquid and the supply of a culture liquid dive an influence to cultivation, it is requested that the exchange and the supply are performed carefully, and that quick exchange processing is performed. However, in respect to problems like this, the patent documents 1 through 3 do not disclose anything. Further, these documents do not disclose or suggest a constitution which solves these problems.

SUMMARY OF THE INVENTION

An object of the present invention, therefore, is to solve the above-mentioned problems, and is to provide a culture chamber using a culture liquid, which is suitable for the cultivation of a culture object such as cells and tissues, a culture apparatus and a liquid supplying method of a culture liquid.

In respect to a constitution of the present invention which solves the above-mentioned problems, explanation is given by enumerating each of technical sides.

In order to attain the above object, a first technical side of the present invention is a culture chamber which cultivates a culture object by using a culture liquid. Its constitution has a culture space part which houses the culture object together with the culture liquid, an introducing part which introduces the culture liquid into the culture space part, a discharging part which discharges the culture liquid from the culture space part, and a flow arrangement part. The flow arrangement part is formed in a side of the introducing part of the culture space part. The flow arrangement part causes a liquid flow, which reaches to the discharging part, to the culture liquid introduced into the culture space part from the introducing part by diffusing from inner wall surfaces of the culture space part toward a direction which intersects a virtual line connecting the introducing part with the discharging part.

By a constitution like this, a Coanda effect which causes a gentle flow to the culture liquid flowing toward the discharging part from the introducing part in the culture space part is obtained, and it is possible to quickly perform an exchange of the culture liquid within the culture space part.

In order to attain the above object, the culture chamber mentioned previously may also be constituted so that the culture chamber has a discharge flow-arrangement part. The discharge flow-arrangement part is formed in a side of the discharging part of the culture space part, and guides the culture liquid, which is led from the inner wall surfaces of the culture space part, to the discharging part. By a constitution like this, it is possible to make the culture liquid discharge to the discharging part from the culture space part calmly.

In order to attain the above object, the culture chamber described previously may also be constituted so that the culture space part includes a first inner wall surface forming a curved surface and a second inner wall surface forming a flat surface formed in a direction which intersects the first inner wall surface. By the second inner wall surface, a parallel flow is caused to the culture liquid, and the Coanda effect is promoted.

In order to attain the above object, the culture chamber described previously may also be constituted so that the culture chamber has a supporting part bridging to a side of the discharging part from the flow arrangement part. By a constitution like this, the culture object is supported with a floating state by the supporting part.

In order to attain the above object, the culture chamber mentioned previously may also be constituted so that the introducing part at a diameter of a passage passing the culture liquid is set smaller than the discharging part.

In order to attain the above object, the culture chamber mentioned previously may also be constituted so that protruding portions are provided at a midway part of the first inner wall surface. By a constitution like this, it is possible to cultivate without contacting the culture object with the inner wall surfaces tightly.

In order to attain the above object, a second technical side of the present invention is a culture apparatus using the culture chamber mentioned previously, and is a constitution in which the culture chamber described previously is provided and the culture object is cultivated. According to a constitution like this, it is possible to exchange the culture liquid of the inside of the culture chamber by a calm flow. Because of this, it is possible to perform a stable cultivation without causing excessive stimulation and/or stress due to a flow of the culture liquid to the culture object.

In order to attain the above object, a third technical side of the present invention is a liquid supplying method of a culture liquid which cultivates a culture object. This liquid supplying method is a constitution comprising guiding the culture liquid, which is introduced into a culture space part housing the culture object, in a direction which intersects its introducing direction, and forming a liquid flow which makes the culture liquid diffuse from inner wall surfaces of the culture space part and makes the culture liquid discharge. By a constitution like this, a calm flow is caused to the culture liquid, and thereby, a Coanda effect is obtained.

The technical features and advantages of the present invention are as in the following.

(1) The gentle exchange of the culture liquid can be performed, and the liquid supply of an exchange of the culture liquid is obtained without giving unnecessary stress, such as a compressive force and a shearing force, to the culture object.

(2) It is possible to perform quickly the exchange of the culture liquid by an injection of the culture liquid of a small quantity.

(3) It is possible to prevent an outflow of a culture object, such as cells and tissues, and an extracellular matrix.

(4) The removal of bubbles in the culture liquid is easy, and it is possible to generate a different liquid flow by the flow rate of the culture liquid.

BRIEF DESCRIPTION OF THE DRAWINGS

The foregoing and other objects, features and attendant advantages of the present invention will be appreciated as the same become better understood by means of the following description and accompanying drawings wherein.

DETAILED DESCRIPTION OF THE PREFERRED EMBODIMENTS

First Embodiment

Figure 1:
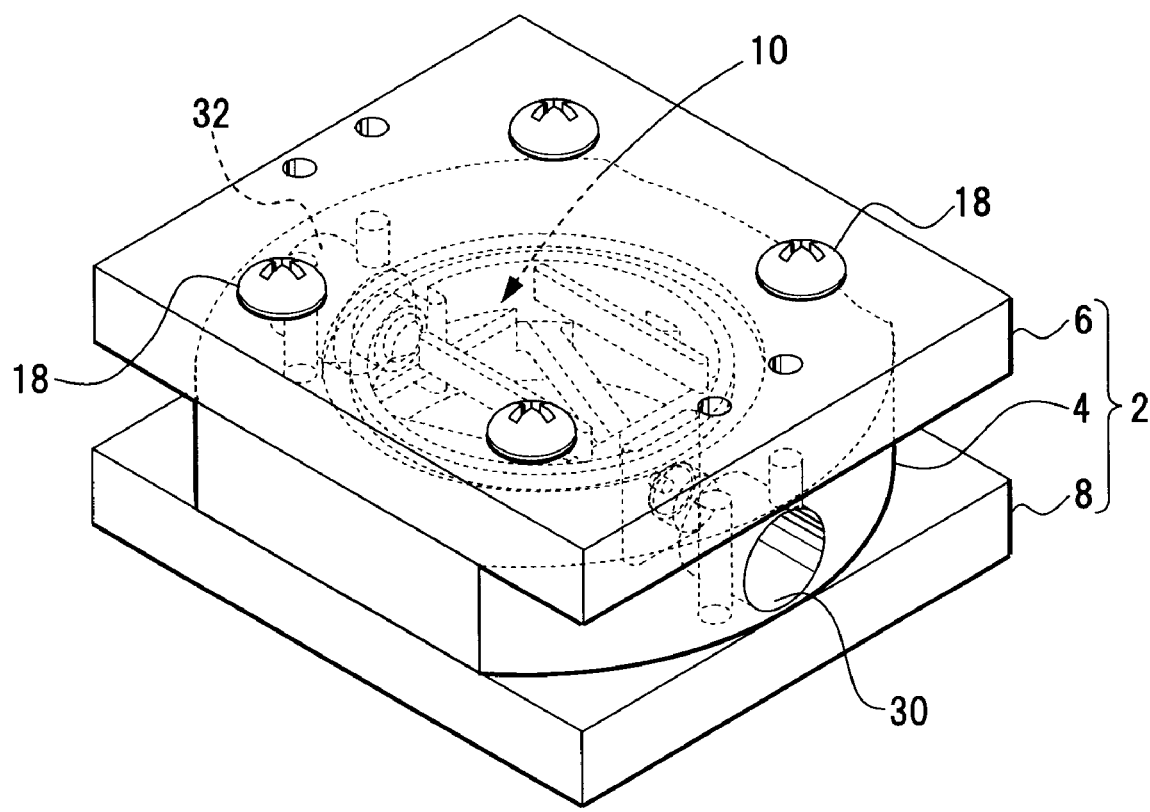
FIG. 1 is a perspective view showing a culture chamber according to a first embodiment.
Figure 2:
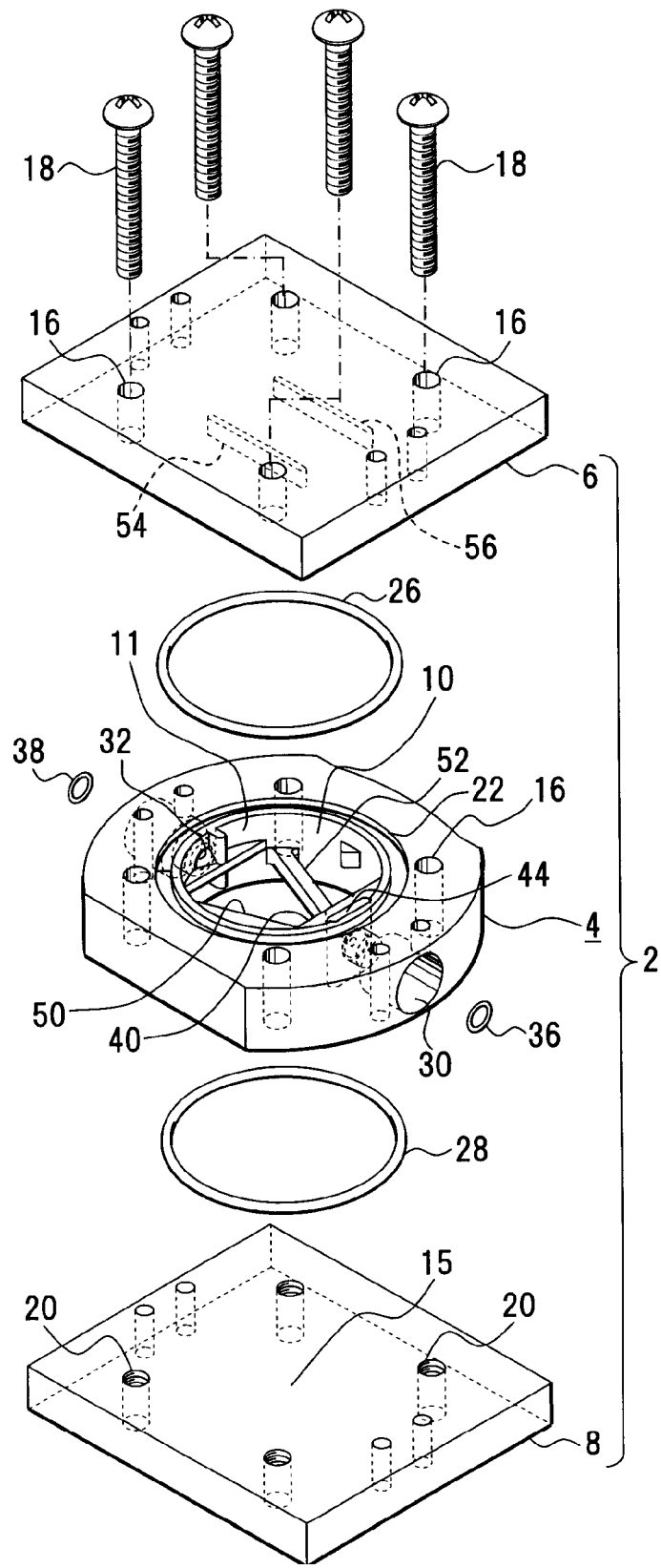
FIG. 2 is an exploded perspective view showing the culture chamber.
Figure 3:
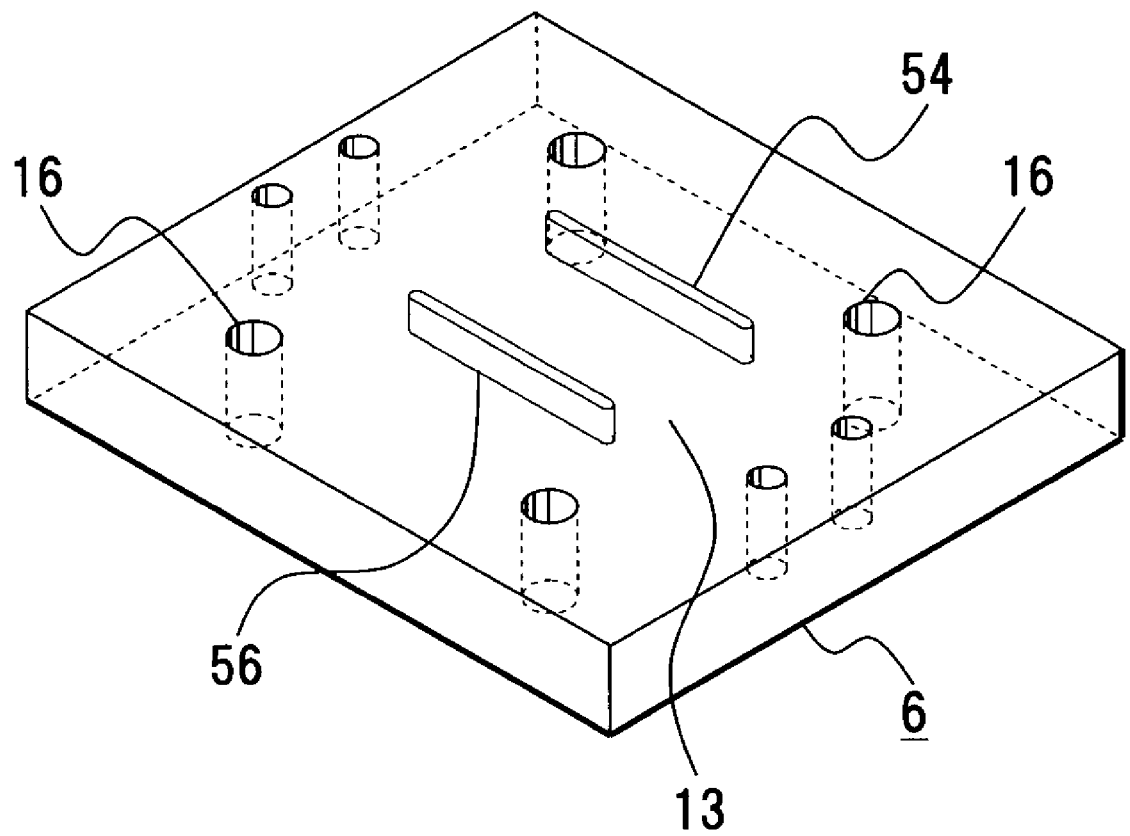
FIG. 3 is a perspective view showing a blockading plate.
Figure 4:
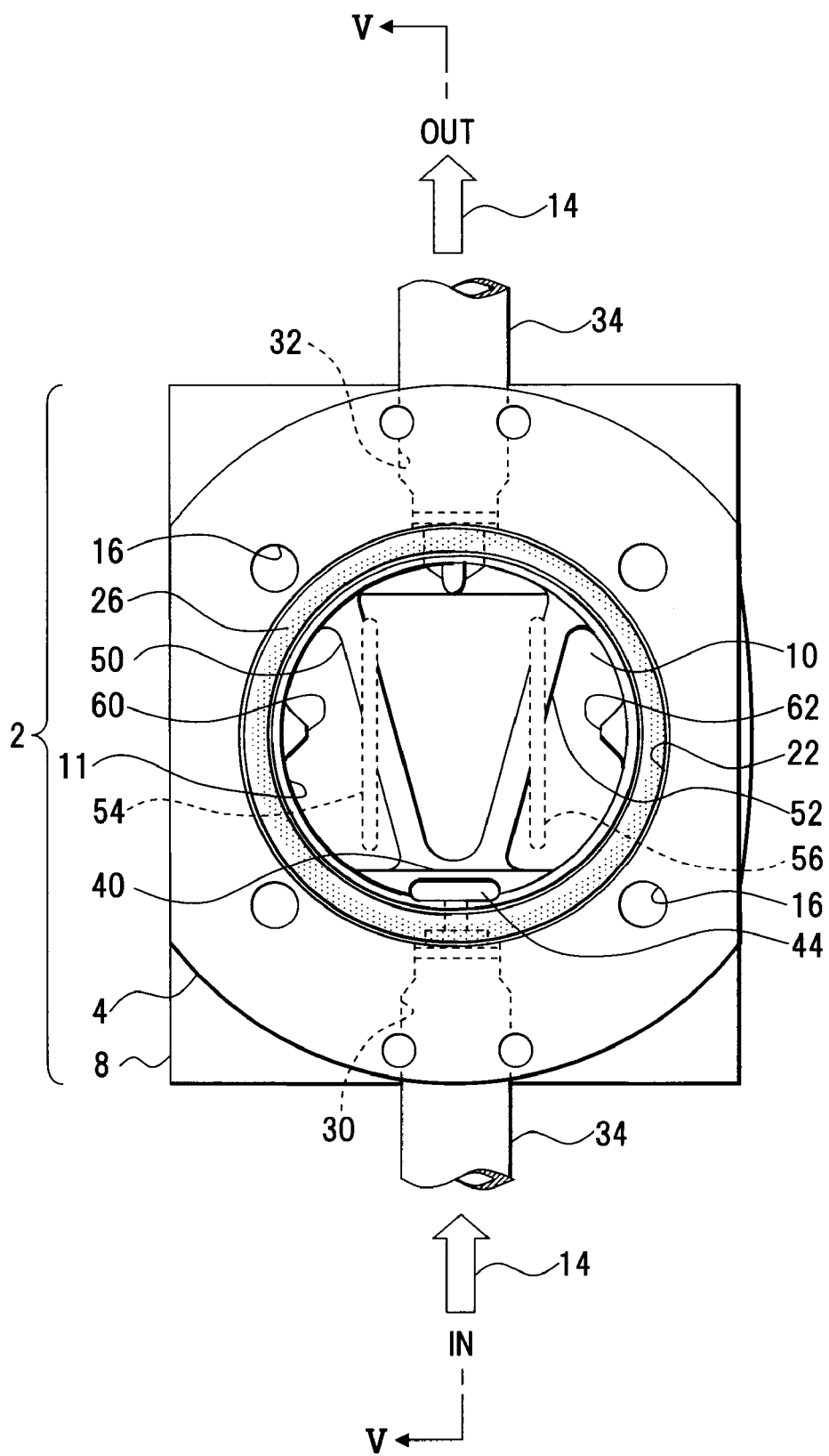
FIG. 4 is a drawing which shows an interior of the culture chamber.
Figure 5:
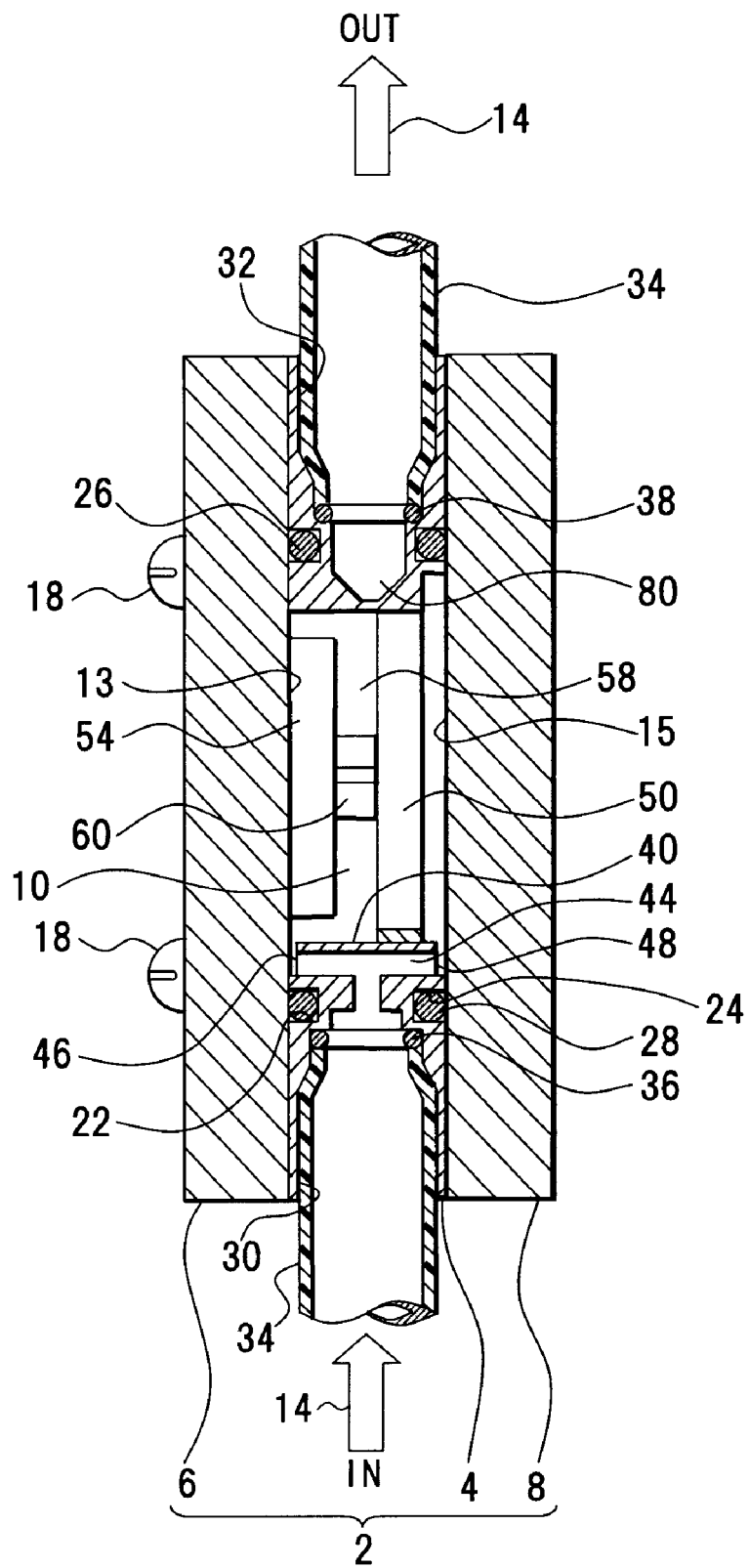
FIG. 5 is a sectional view taken along line V-V of FIG. 4.

A first embodiment of the present invention is explained by referring to FIG. 1, FIG. 2, FIG. 3, FIG. 4 and FIG. 5. FIG. 1 is a perspective view showing a culture chamber, FIG. 2 is an exploded perspective view showing the culture chamber, FIG. 3 is a perspective view showing one blockading plate, FIG. 4 is a drawing which shows the culture chamber under a state that a blockading plate is removed, and FIG. 5 is a sectional view taken along line V-V of FIG. 4.

This culture chamber 2 has a main body part 4 which is constituted by a cylindrical body, and also has first and second blockading plates 6 and 8 which blockade the main body part 4. By these, the culture chamber 2 constitutes a cylinder-shaped culture space part 10. That is, this culture space part 10 is constituted by a first inner wall surface 11 consisting of a curved surface of a circular shape, which is constituted by the main body part 4, and inner wall surfaces 13 and 15 as a second inner wall surface constituting a flow arrangement part. The inner wall surface 13 (FIG. 3) forms a flat surface of the blockading plate 6, and the inner wall surface 15 forms a flat surface of the blocking plate 8. A culture object 12 (FIG. 10), such as cells and tissues of a living body, and a culture liquid 14 are housed in this culture space part 10. The main body part 4 and the blockading plates 6 and 8 are constituted by stainless steel or glass, for example. For example, the main body part 4 and the blockading plates 6 and 8 are unified as follows. Bolts 18 are made to penetrate a plurality of through holes 16 which are formed in the main body part 4 and the blockading plate 6, and these bolts 18 are screwed into tapped holes 20 which are formed in a side of the blockading plate 8. By this, the main body part 4 and the blockading plates 6 and 8 are fixed in a body so that the main body part 4 is sandwiched between the blockading plates 6 and 8, and the culture space part 10 is formed by the inner wall surface 111 formed in the main body part 4 and the inner wall surfaces 13 and 15 of the blockading plates 6 and 8. In contact surface parts of each of the blockading plates 6 and 8 of the main body part 4, groove portions 22 and 24 (FIG. 5) which circle the culture space part 10 are formed. In these groove portions 22 and 24, O-rings 26 and 28 are positioned, and are sandwiched into portions between the main body part 4 and the blockading plates 6 and 8 respectively. Thereby, the culture space part 10 is shielded.

In the main body part 4, an introducing port 30 is formed as an introducing part which introduces a culture liquid 14 into the culture space part 10, and a discharging port 32 is formed as a discharging part which discharges the culture liquid 14 from the culture space part 10. These introducing port 30 and discharging port 32 are opposed each other with the culture space part 10 as a center, and are also formed in a direction which is at right angles with a central direction of the culture space part 10. To the introducing port 30 and the discharging port 32, a circulating pipe 34 for the culture liquid 14 are coupled, and O-rings 36 and 38 which shields those coupled portions are provided.

In the culture space part 10 of the main body part 4, as the flow arrangement part which arranges a liquid flow of the culture liquid 14, a vertical wall 40 is formed at the side of an opening portion of the introducing port 30, and a small space part 44 which is surrounded by the vertical wall 40 and the inner wall surface 11 of the culture space part 10 is also formed. Further, at portions between the small space part 44 and the inner wall surfaces 13 and 15 of the blockading plates 6 and 8, slit portions 46 and 48 (FIG. 5) are formed. That is, the small space part 44 is communicated with the culture space part 10 through the slit portions 46 and 48, and the culture liquid 14 which is introduced from the introducing port 30 is guided to an inside of the culture space part 10 from the small space part 44 by way of the slit portions 46 and 48.

In the culture space part 10, as a supporting part which supports the culture object 12, a pair of supporting bars 50 and 52 formed into a V-shape, which bridges between the vertical wall 40 of the small space part 44 and a wall surface part opposite to the vertical wall 40, is provided. These supporting bars 50 and 52 are provided at a position displaced to the side of the blockading plate 8 from a central part of the direction of a depth of the culture space part 10, and form a surface parallel to the blockading plates 6 and 8. As a supporting part opposite to these supporting bars 50 and 52, a pair of vertical walls 54 and 56 is provided on the blockading plate 6. A gap part 58 (FIG. 5) is formed between the supporting bars 50 and 52 and the vertical walls 54 and 56, and the culture object 12 is disposed in the gap part 58. Further, in the inner wall surface 11 of the culture space part 10 surrounding the gap part 58, chevron-shaped protruding portions 60 and 61 are formed face to face so that the culture object 12 does not come into tight contact with the inner wall surface 11.

Figure 6:
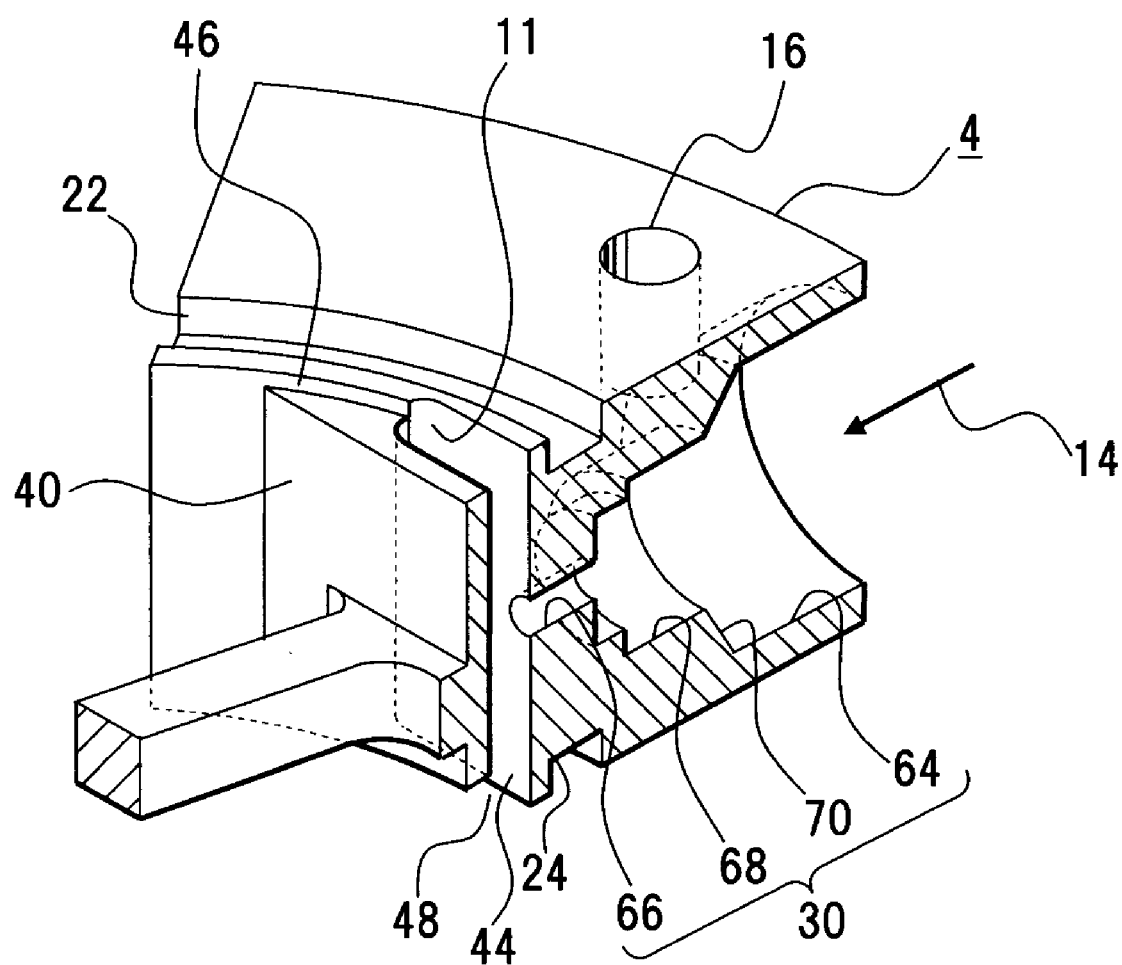
FIG. 6 is a perspective view showing a part of a main body part in which a part of an introducing port is cut off.
Figure 7:
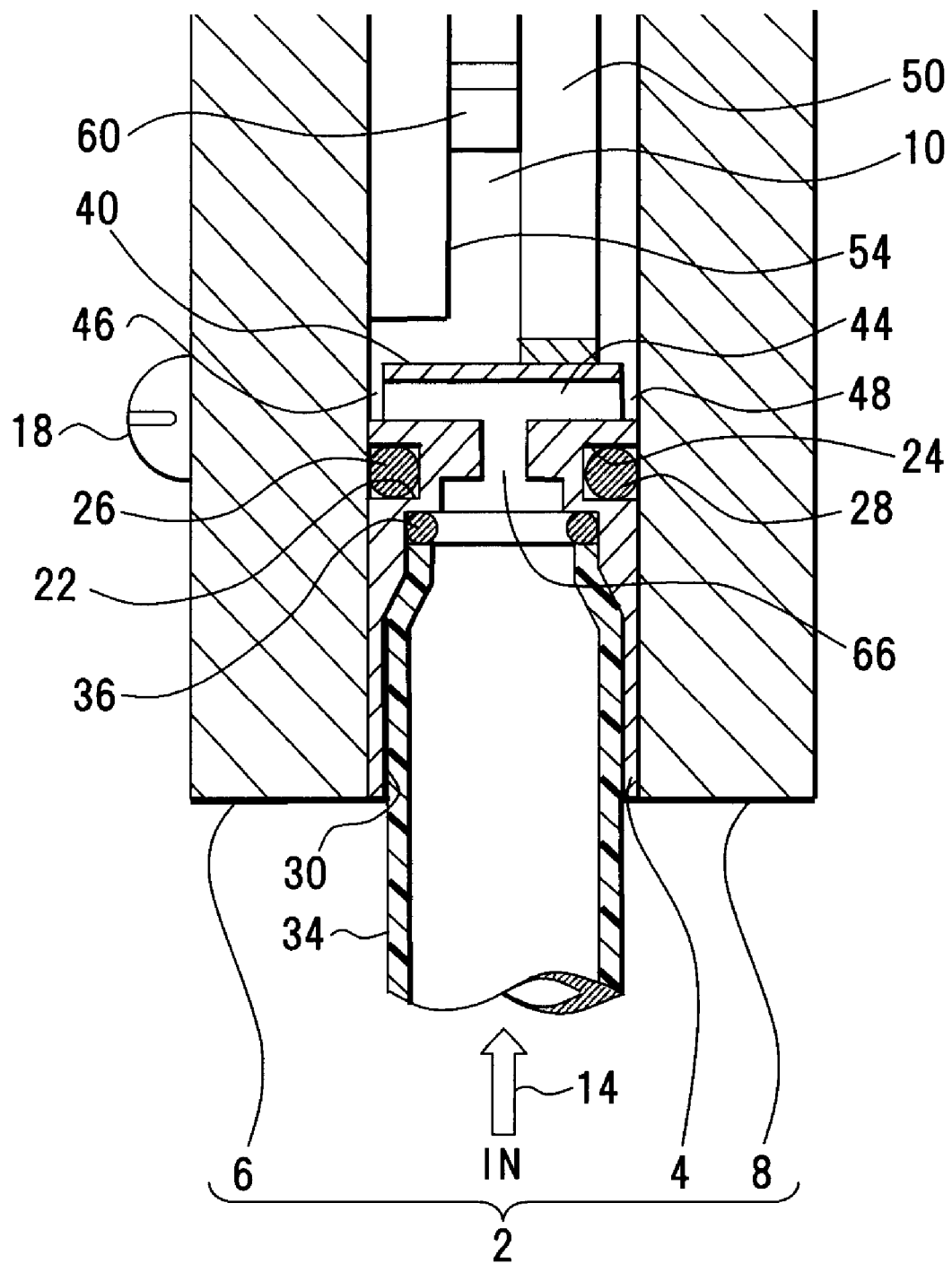
FIG. 7 is a sectional view showing a part of the main body part in which the part of the introducing port is cut off.

The constitution of the introducing port 30 of the culture chamber 2 is explained by referring to FIG. 6 and FIG. 7. FIG. 6 is a perspective view showing the introducing port 30 and its adjacent part which is cut off, and FIG. 7 is a sectional view showing an adjacent part of the introducing port 30 together with the blockading plates.

The introducing port 30 is a through hole which is formed in the main body part 4 in an orthogonal direction with the culture space part 10. The introducing port 30 has a large-diameter hole portion 64 at the side of an outer wall surface of the main body part 4 and a nozzle hole portion 66 with a small diameter at the side of its inner wall surface. Diameters of an intermediate portion between the large-diameter hole portion 64 and the nozzle hole portion 66 are different in a staircase form. Along with this, an intermediate hole portion 68, at which an O-ring 36 is provided, and a cone-shaped hole portion 70 are formed.

Further, a height of the vertical wall 40 forming the small space part 44 is set slightly smaller than a height of the culture space part 10, and the slit portions 46 and 48 are formed in order to guide the culture liquid 14 from the small space part 44 to the culture space part 10.

Figure 8:
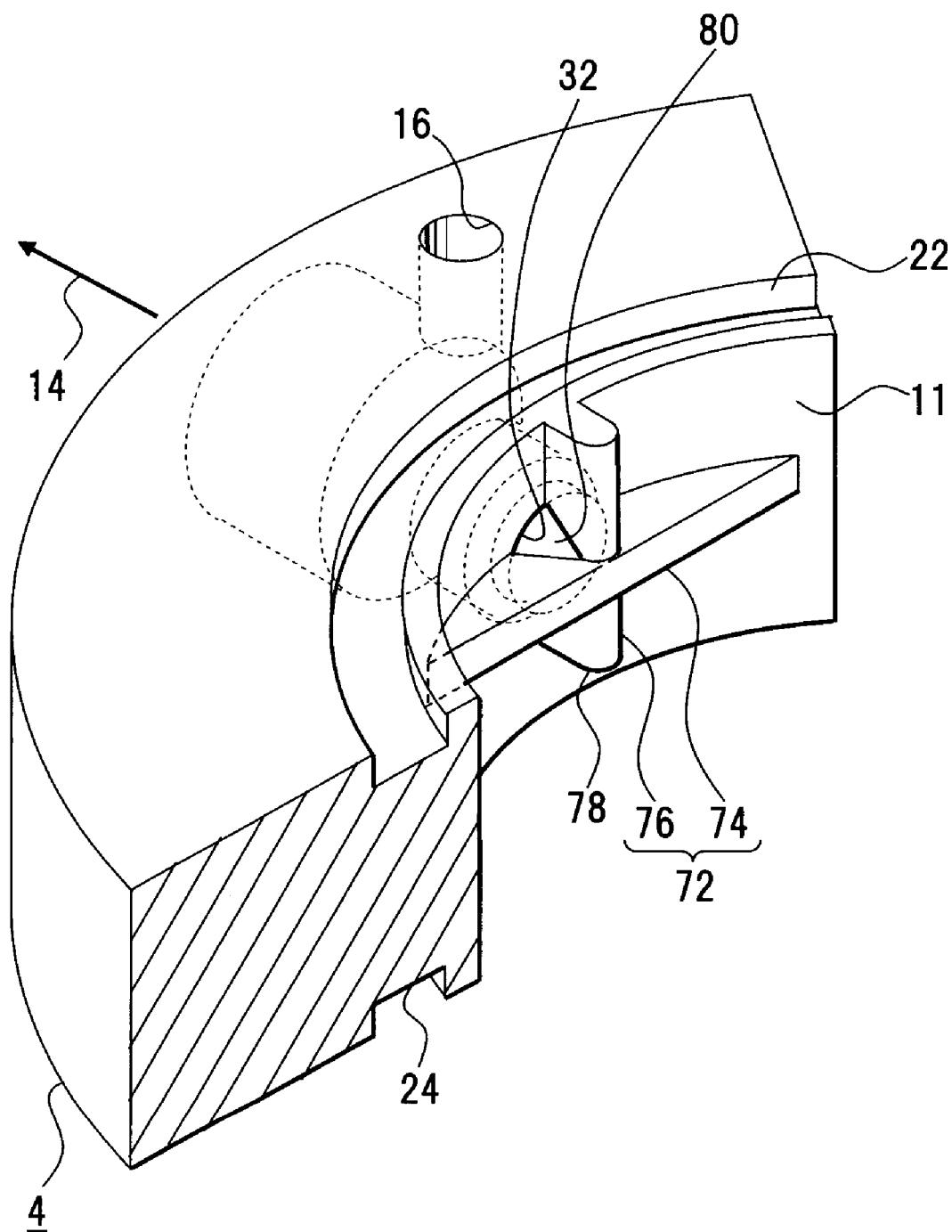
FIG. 8 is a perspective view showing a part of the main body part in the case of looking a part of a discharging port from a culture space part.
Figure 9:
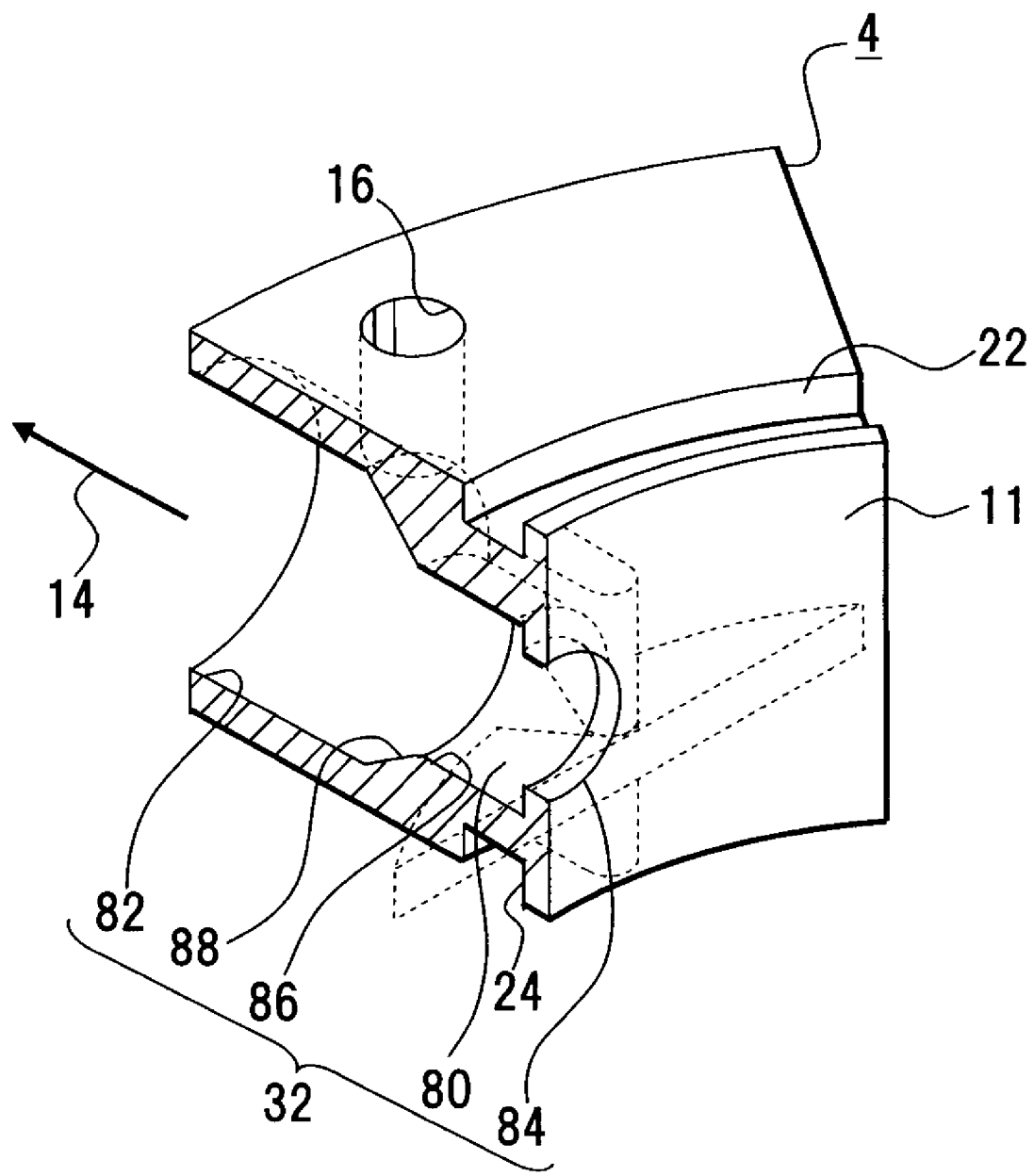
FIG. 9 is a perspective view showing a part of the main body part in which the part of the discharging port is cut off.

The constitution of a side of the discharging port 32 of the culture chamber 2 is explained by referring to FIG. 8 and FIG. 9. FIG. 8 is a drawing which shows the part of the discharging port in the case of looking from the side of the culture space part, and FIG. 9 is a perspective view showing a section of the discharging port.

In a surrounding part of the discharging port 32, as a discharge flow-arrangement part, a grid-shaped vertical wall 72 which intersects with each other at the central part of the discharging port 32 is formed. This vertical wall 72 is constituted by a vertical wall part 74, which is formed in a direction parallel to the supporting bars 50 and 52, and a vertical wall part 76 which meets at right angles with the vertical wall part 74. One end face 78 of the vertical wall part 76 is formed on the same face with the supporting bars 50 and 52 (FIG. 5). Further, at a part of the vertical wall 72 opposite to the discharging port 32, a notch portion 80 composed of a curved surface is formed in order to expand an entrance part of the discharging port 32.

Further, the discharging port 32 is a through hole which is formed in the main body part 4 in an orthogonal direction with the culture space part 10. The discharging port 32 has a large-diameter hole portion 82 at the side of the outer wall surface of the main body part 4 and a small-diameter hole portion 84 at the side of the inner wall surface of the main body part 4. Diameters of an intermediate portion between the large-diameter hole portion 82 and the small-diameter hole portion 84 are different in a staircase form. Along with this, an intermediate hole portion 86, at which an O-ring 38 is provided, and a cone-shaped hole portion 88 are formed.

Figure 10:
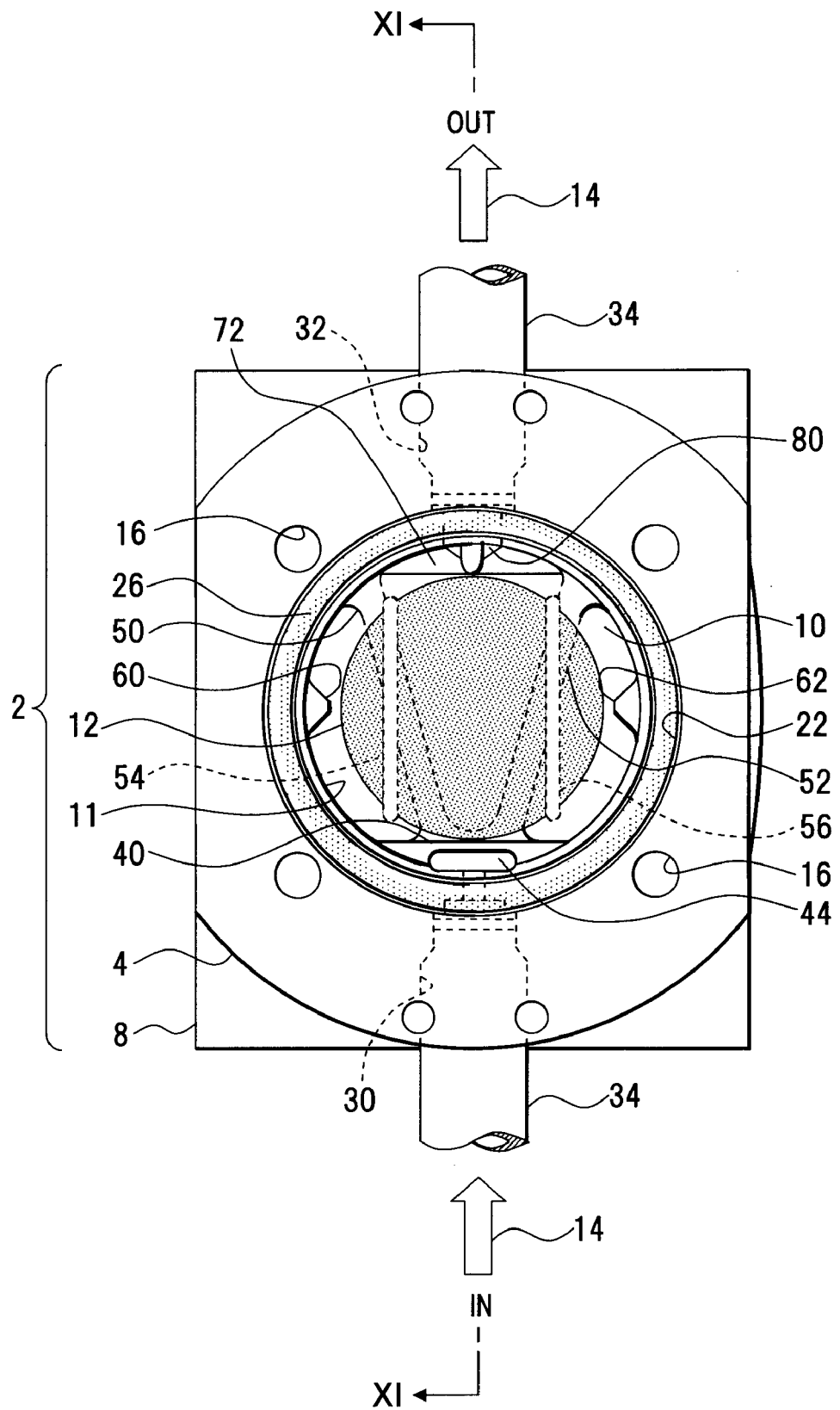
FIG. 10 is a plan view showing the culture chamber in which a culture object is placed.
Figure 11:
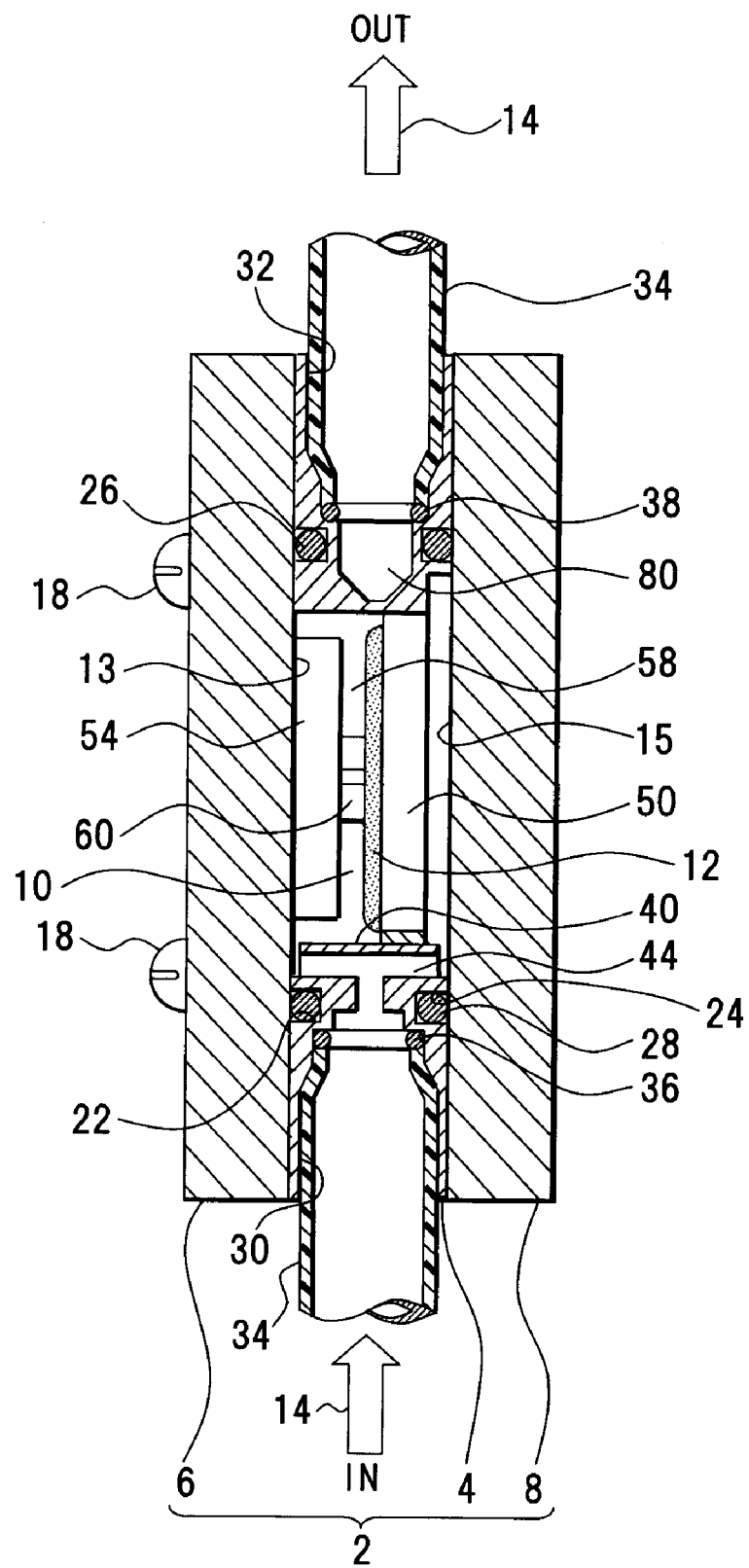
FIG. 11 is a sectional view taken along line XI-XI of FIG. 10.

Furthermore, as shown in FIG. 10 (the culture chamber 2 shown under a state that the blockading plate 6 is removed) and FIG. 11 (a sectional view taken along line XI-XI of FIG. 10), in the culture space part 10 of the culture chamber 2, the culture object 12 is arranged in a space part, which is surrounded by the protruding portions 60 and 62, the supporting bars 50 and 52 and the vertical walls 54 and 56, without coming into tight contact with the inner wall surfaces 11, 13 and 15, and is kept to be maintained with a floating state.

Figure 12:
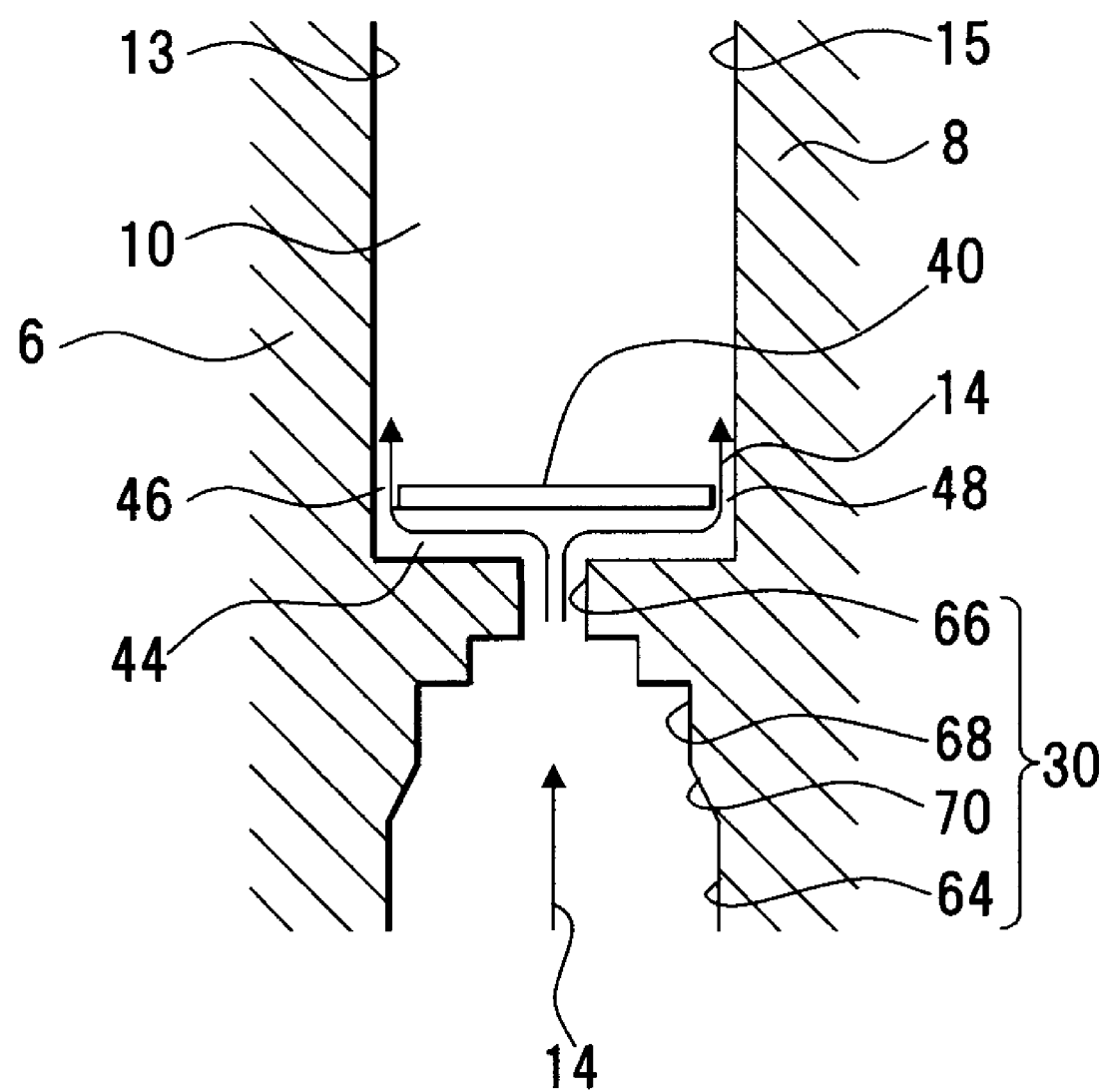
FIG. 12 is a drawing which shows a flow of a culture liquid at the part of the introducing port.
Figure 13:
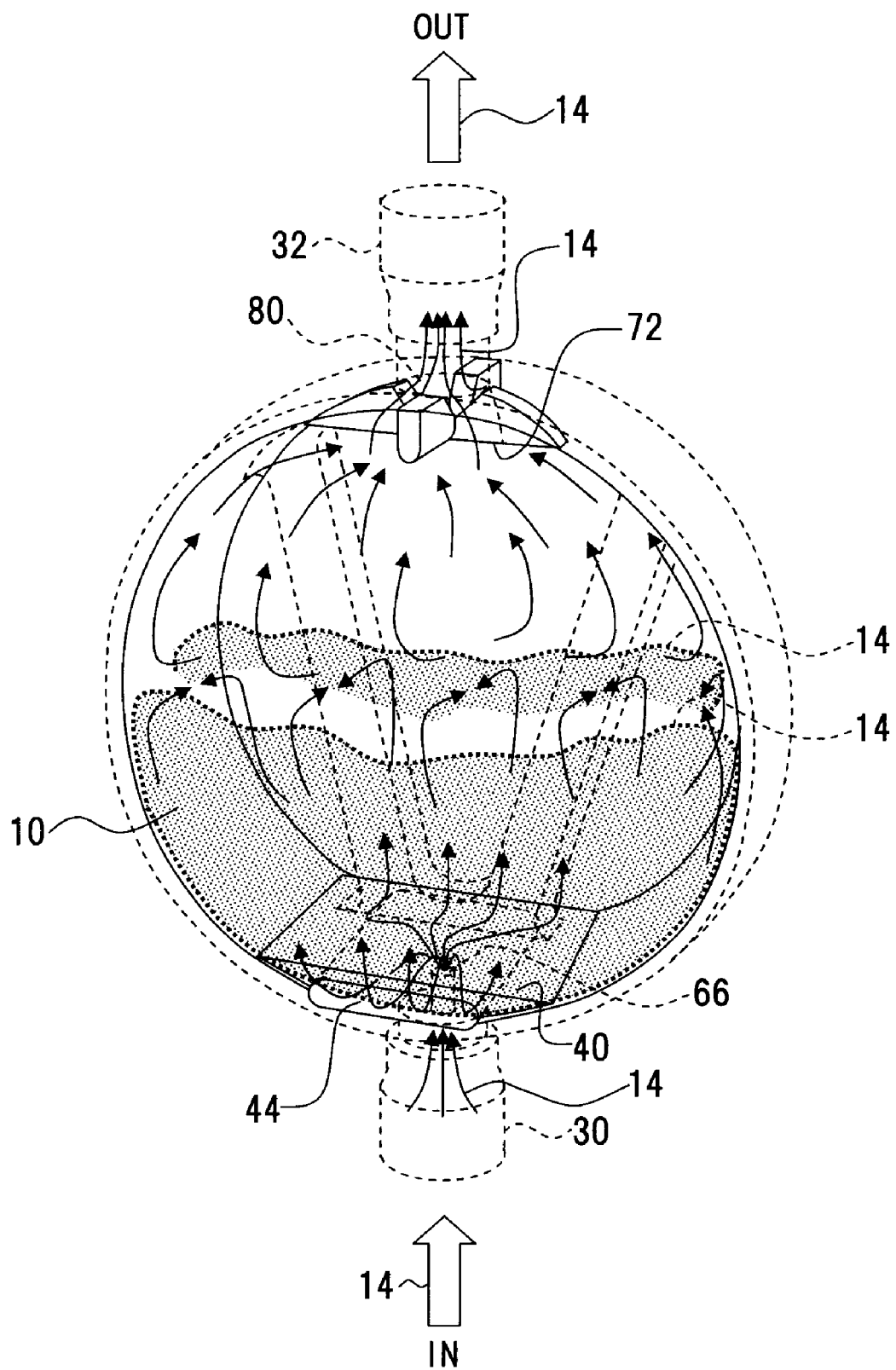
FIG. 13 is a drawing which shows a flow of the culture liquid in the culture space part.
Figure 14:
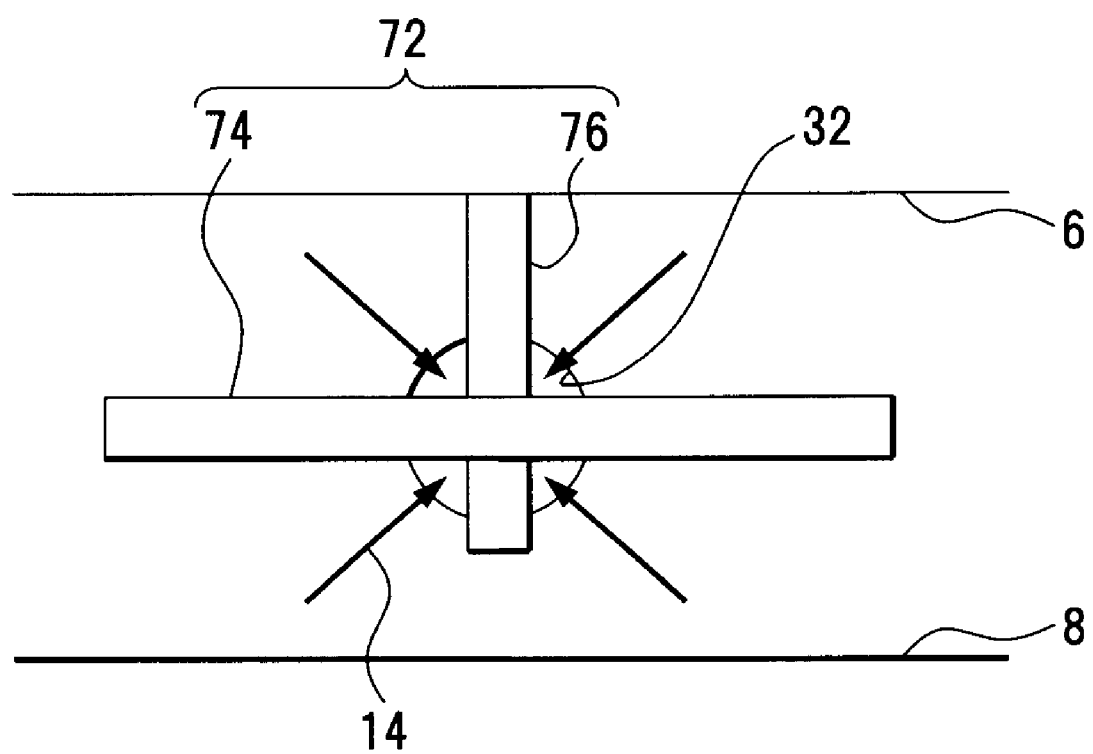
FIG. 14 is a drawing which shows a flow of the culture liquid at the part of the discharging port.

Next, a liquid supplying method and a flow of the culture liquid 14 in the culture chamber 2 are explained by referring to FIG. 12, FIG. 13 and FIG. 14. FIG. 12 is a drawing showing a flow of the culture liquid which reaches the culture space part from the introducing port and the small space part, FIG. 13 is a drawing which shows a flow of the culture liquid in the culture space part, and FIG. 14 is a drawing showing a flow of the culture liquid which reaches the discharging port from the culture space part.

As shown in FIG. 12, the culture liquid 14 which is introduced into the culture space part 10 from the introducing port 30 becomes faster in its flow velocity because an opening diameter narrows toward the nozzle hole portion 66 from the large-diameter hole portion 64, and reaches the small space part 44. By the vertical wall 40 existing at a front part of the nozzle hole portion 66, the culture liquid 14 is reduced in its flow velocity, and is guided to the side of the slit portions 46 and 48. By this, a flow along the inner wall surfaces 13 and 15 from the slit portions 46 and 48 occurs, and this flow is to run along the inner wall surface 11 of the culture space part 10.

As shown in FIG. 13, in the culture space part 10, the culture liquid 14 moves along the inner wall surfaces 13 and 15 by the Coanda effect. The culture liquid 14 moving along the inner wall surfaces 13 and 15 is gradually diffused into the culture liquid 14 of the inside of the culture space part 10 and is mixed in it while slowing down the velocity gradually.

Then, the culture liquid 14 in the culture space part 10 flows toward the discharging port 32. As shown in FIG. 14, since the grid-shaped vertical wall 72 exists in the vicinity of the discharging port 32, the culture liquid 14 is discharged from the discharging port 32 formed small at its orthogonal part.

The flow velocity of the culture liquid 14 is smaller than a critical Reynolds number, and is very slow. Because of this, the culture liquid 14 which is given by inflow maintains a laminar flow state to flow. Along with this, the culture liquid 14 given by the inflow is gradually diffused into the culture liquid 14 which is already filled, and mixes into the culture liquid 14 which exists there. Then, the culture liquid 14 of a quantity equivalent to the culture liquid 14 which is given by inflow is discharged from the culture space part 10.

Figure 15A:
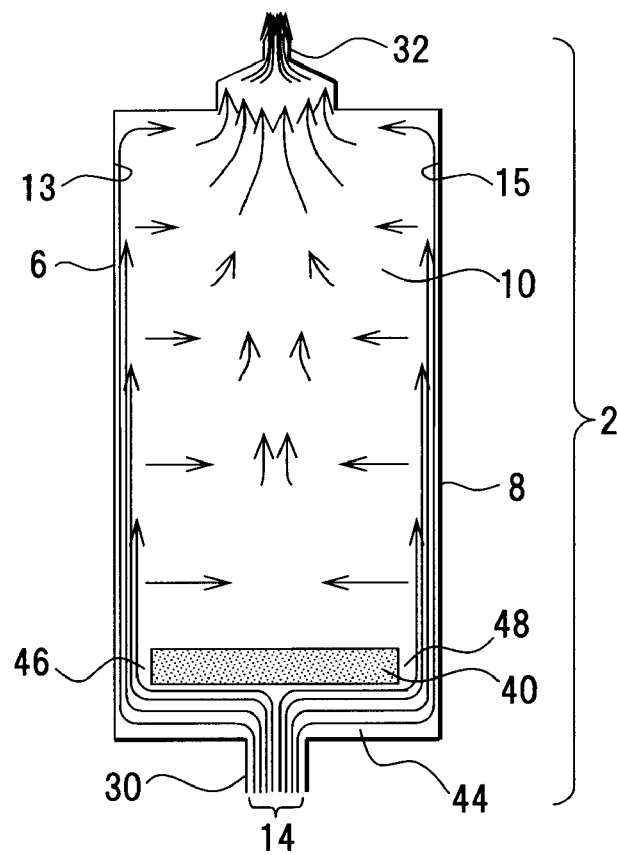
FIG. 15A and FIG. 15B are drawings which show a flow of the culture liquid in the culture space part.
Figure 15B:
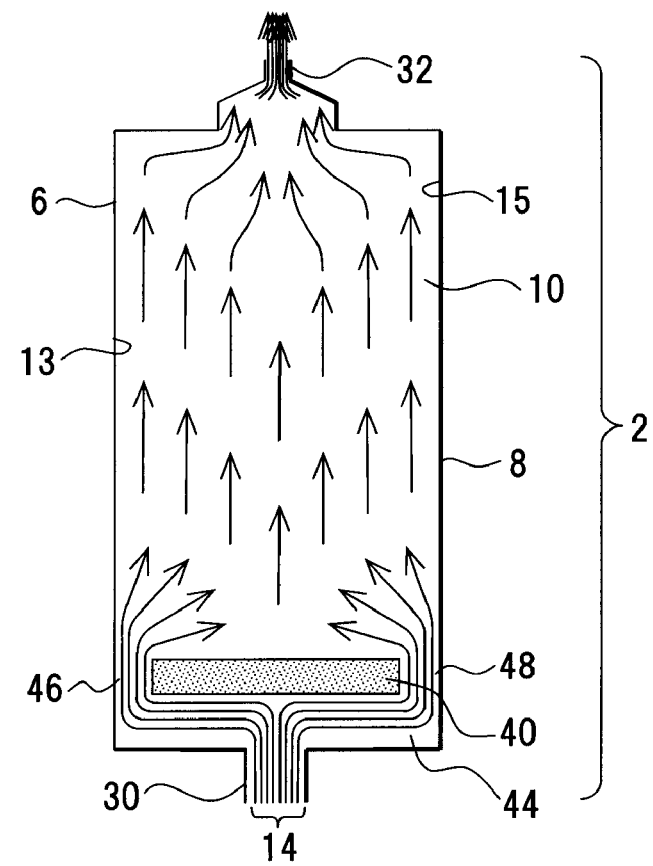
Figure 16:
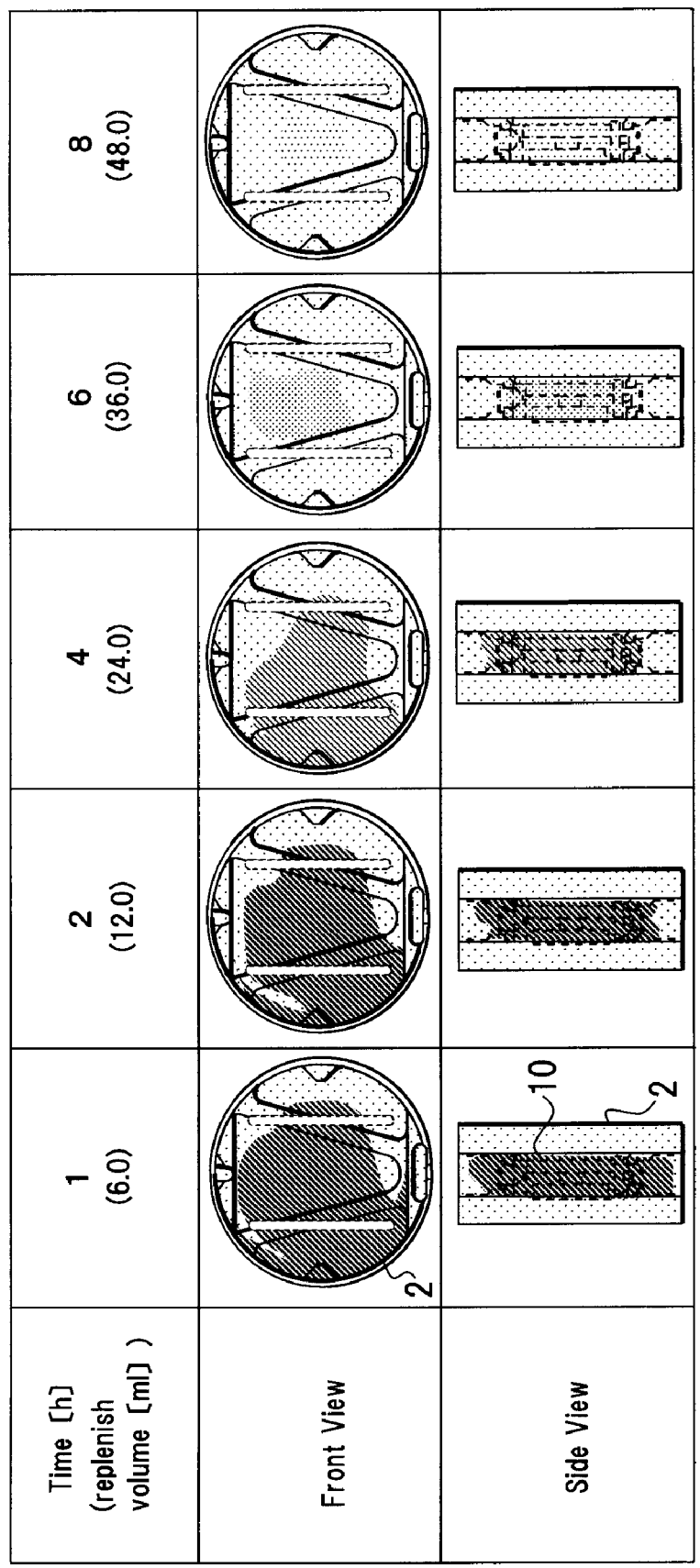
FIG. 16 is a drawing which shows a state of an exchange of the culture liquid.
Figure 17:
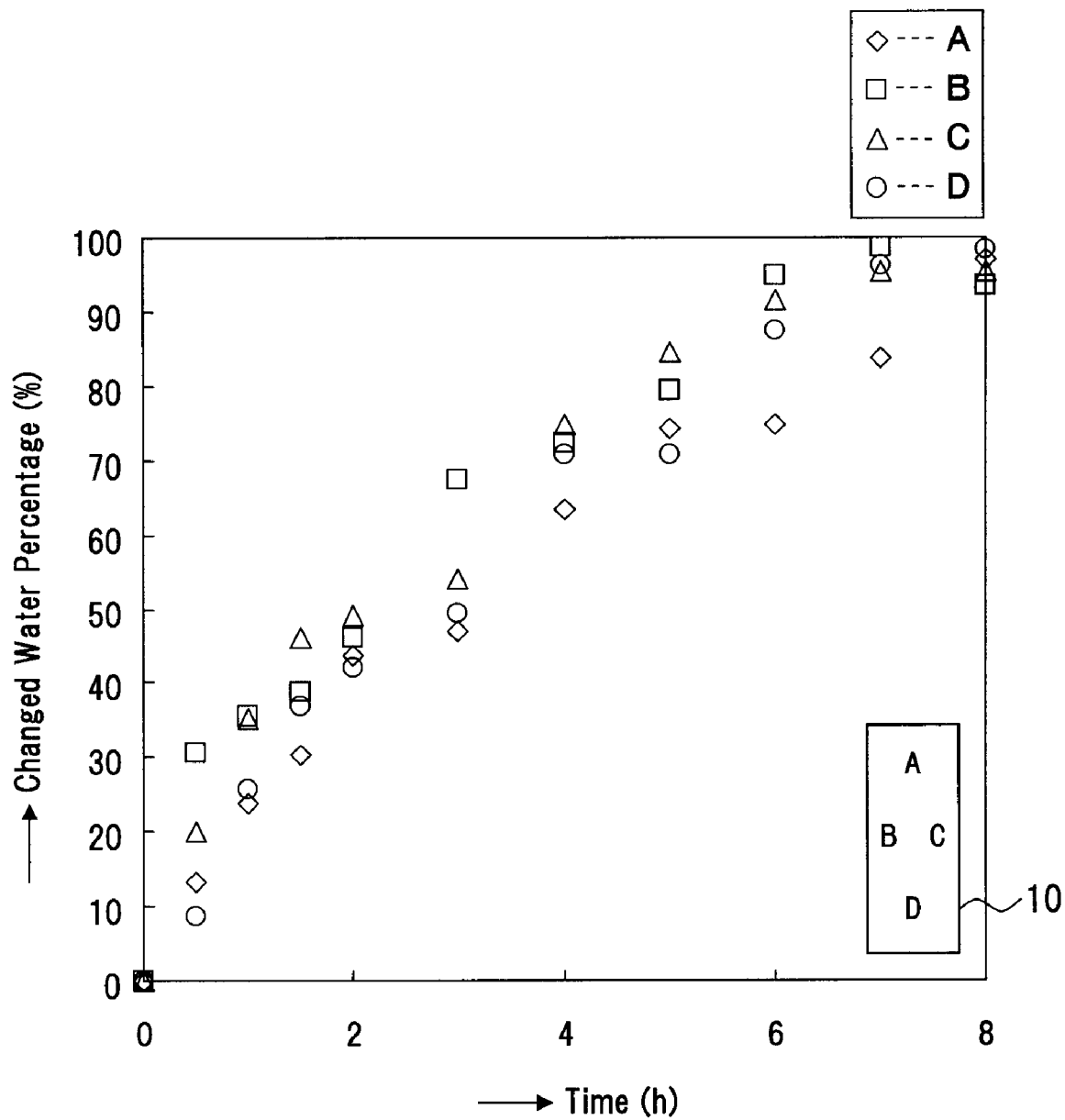
FIG. 17 is a drawing which shows a state of an exchange of the culture liquid.
Figure 18:
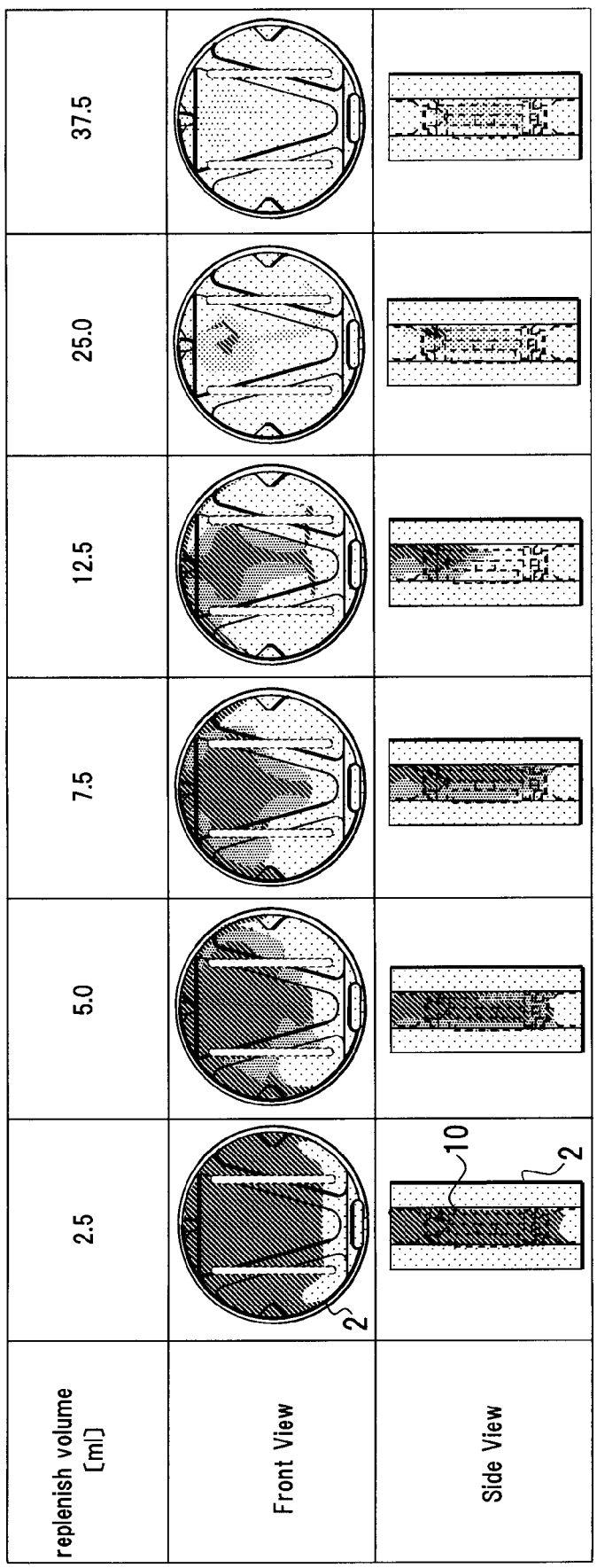
FIG. 18 is a drawing which shows a state of an exchange of the culture liquid.
Figure 19:
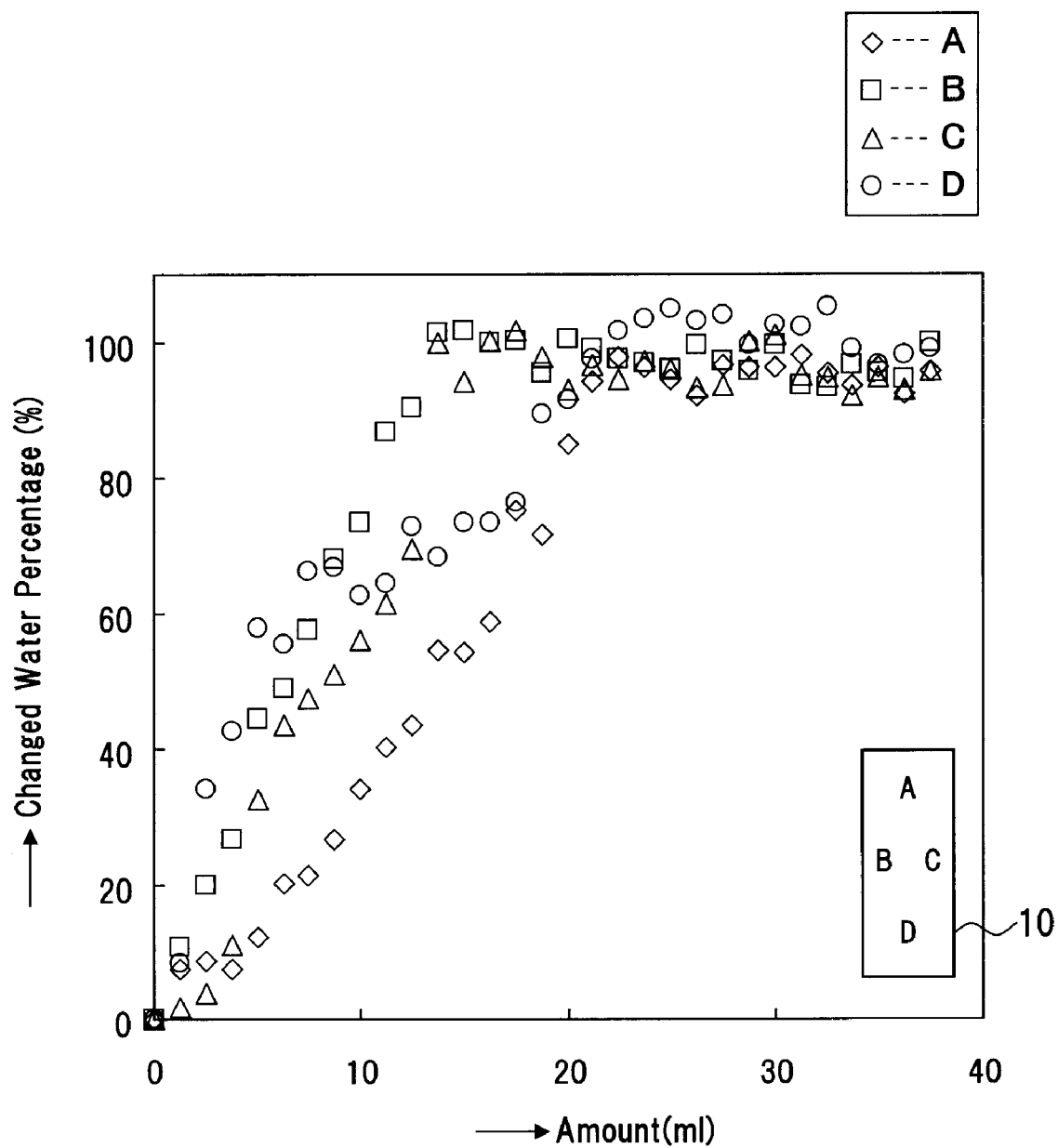
FIG. 19 is a drawing which shows a state of an exchange of the culture liquid.

Next, an exchange function of the culture liquid 14 of the culture chamber 2 is explained by referring to results of experiments shown in FIG. 15A, FIG. 15B, FIG. 16, FIG. 17, FIG. 18 and FIG. 19. FIG. 15A and FIG. 15B are drawings which are an overall flow of the culture liquid in the culture space part. FIG. 16 is a drawing showing the state of affairs, in which the culture liquid corresponding to FIG. 15A is exchanged, in time-series. FIG. 17 is a drawing showing a change in an exchange of the culture liquid in each part of the culture space part corresponding to FIG. 15A. FIG. 18 is a drawing showing the state of affairs, in which the culture liquid corresponding to FIG. 15B is exchanged, in time-series. FIG. 19 is a drawing showing a change in an exchange of the culture liquid in each part of the culture space part corresponding to FIG. 15B.

In an experiment, an internal diameter of the main body part 4 of the culture chamber 2 is set to 36 [mm], its depth is set to 15 [mm], and the culture object 12 is disposed therein. In this case, the volume of the culture space part 10 is approximately 15 [ml]. In the culture chamber 2, the culture object 12 is in a state that the culture object 12 is floated in the culture liquid 14 which is filled in the culture space part 10. The flow of the culture liquid 14 is as mentioned previously. Trying to put the culture liquid 14 of 15 [ml], which is a quantity equivalent to the volume of the culture space part 10 of the culture chamber 2, into the culture space part 10 in 2.5 hours, the flow rate of 100 [µl/min] becomes necessary.

In the case of changing the flow velocity of the culture liquid 14, when the flow velocity is slow (when the flow rate per unit time is few), as shown in FIG. 15A (the flow of the culture liquid 14 in the section shown in FIG. 5), a laminar flow along the sides of the inner wall surfaces 13 and 15 of the blockading plates 6 and 8 is formed. That is, the culture liquid 14 injected into the introducing port 30 reaches the inner wall surfaces 13 and 15 of the culture space part 10. After that, the culture liquid 14 flows so that a thin film drifts along the inner wall surfaces by the Coanda effect, but the culture liquid 14 does not flow into the central part directly. In the flow rate of the flow velocity which is very slow, since a Reynolds number is smaller than the critical Reynolds number by far, the laminar flow is maintained. Because of this, the flow is not disarranged even when hitting against the inner wall surfaces, and the culture liquid 14 flows along the inner wall surfaces because a fluid has a character flowing along a wall. Since the culture liquid 14 is the laminar flow, frictional resistance is large. Because of this, the culture fluid 14 drifts so as to stick to the inner wall surfaces, and its flow velocity is lost. After that, the culture liquid 14 which is new is gradually diffused into the culture liquid 14 which is filled, and the culture liquid 14 is gradually shifted to the culture liquid 14, which is fresh, toward the side of the culture object 12 from the side of the inner wall surfaces of the culture space part 10.

Further, if the flow rate of the culture liquid 14 is increased, for example, in the case of setting the flow late of 1000 [µl/min], the culture liquid 14 comes into a flow shown in FIG. 15B. That is, the culture liquid 14 introduced into the small space part 44 flows through the slit portions 46 and 48 as passages. At that time, according as the flow rate increases, the culture liquid 14 comes into the flow which spreads from the slit portions 46 and 48. Because of this, a flow turning into the vertical wall 40 also occurs, and a flow which fans out between the vertical wall 40 and the inner wall surfaces 13 and 15 of the culture space part 10 also occurs. Even if the flow velocity is 1000 [µl/min], the Reynolds number is low, for example, a level of 20. The flow is not disarranged because the flow is the laminar flow, and the flow tube of a fluid enlarges largely in a diameter. Since a sectional area of the flow tube enlarges rapidly, the flow velocity further lowers by the theory of continuity. Because of this, its flow velocity is lost, and the culture liquid 14 which is newly introduced is to accumulate at the side of a bottom part.

The experimental results corresponding to the flow velocity shown in FIG. 15A and FIG. 15B are explained. In the case of FIG. 15A, as shown in FIG. 16 and FIG. 17, the diffusion of the culture liquid 14 occurs from the sides of the inner wall surfaces of the culture space part 10 gradually, and it is shifted to the central part presently. FIG. 17 shows the transition of the exchange of the culture liquid 14 in respect to four points of the culture space part 10, namely the points of A (=the part of the discharging port 32), B (=the wall surface of the side of the blockading plate 6), C (=the wall surface of the side of the blockading plate 8) and D (=the part of the introducing port 30). Further, FIG. 18 and FIG. 19 show the experimental result corresponding to FIG. 15B. In this case, the culture liquid 14 shifts to the culture liquid 14, which is new, from the lower side of the culture space part 10, its new part and its old part forms a layer to move, and the culture liquid 14 which is old is discharged so that it is pushed out from the discharging port 32. Because of this, at the time that the amount of flow of one and a half times is introduced into the culture space part 10, the culture liquid 14 is to be almost exchanged for the culture liquid 14 which is new.

Such a flow of the culture liquid 14 is similar to a flow of a liquid in a fluid control device which is used for the control of a fluid. In the fluid control device, a fluid flows in a direction of either one of two directions which branch into a Y-shape, and the flow is changed in another direction if a some action is given to the flow at a point before the Y-shape. It will be understood that, according to the inside constitution of the culture space part 10, by changing the flow rate, the flow along a specific wall surface occurs, or a laminar flow pattern which is changed into the flow diffusing in the flow tube formed by a plurality of wall surfaces occurs. Even if a laminar flow pattern like this occurs, stimulation and/or stress is not given to the culture object 12 under cultivation because the flow velocity is low. That is, it has been confirmed by an experiment that unnecessary stress such as shearing stress caused by a conventional cultivation hardly occurs.

Furthermore, the side of the discharging port 32 is once reduced from a large diameter to a small diameter, and has the grid-shaped vertical wall 72 at a portion before the large diameter. By this, a fast part of the flow velocity is designed not to approach the culture object 12. What is more, since the discharging port 32 is divided into the four parts by the vertical wall 72, sucking pressure does not come into a strong state if one of these is blocked. Because of this, the culture object 12 and so on are not sucked into the side of the discharging port 32, and do not flow out of the culture space part 10. That is, there is nothing to cause a circling flow such as a swirl by the culture liquid 14 which flows out from the side of the discharging port 32. In addition, it is possible to make bubbles mixing into the culture space part 10 flow out from the discharging port 32 of the large diameter.

Enumerating the featured matters of this embodiment, these are as in the following.

(1) It is possible to control the exchange of the culture liquid 14 in the culture chamber 2, and to perform so as not to give any stress to the culture object 12 at the time of the exchange of the culture liquid 14.

(2) It is possible to pour the culture liquid 14, which is introduced, along the inner wall surfaces by utilizing the Coanda effect, and to make it diffuse from there.

(3) As mentioned later, this culture chamber 2 is suitable for a circulation of the culture liquid 14, in which a closed circuit is formed in order to perform a stable exchange of the culture liquid 14 and a pump able to supply the liquid of a predetermined quantity is used.

(4) Since the culture object 12 is not exposed to a jet flow which is fast in the flow velocity, it is possible to perform a stable cultivation.

(5) The small space part 44 is pre-set, and the culture liquid 14 is poured into the culture space part 10 little by little through the slit portions 46 and 48 serving as spouting ports. By this, the exchange of the culture liquid 14 is realized.

(6) By increasing the flow rate of the culture liquid 14, the flow tube is enlarged in diameter, and the flow velocity is decreased by enlarging in diameter. By this, it is possible to shift into the culture liquid 14, which is new, from the lower part of the culture space part 10 slowly.

(7) In the side of the discharging port 32 the passage of the large diameter is set, and thereby, the flow velocity of the culture liquid 14 is reduced. In this case, the grid-shaped vertical wall 72 is provided, and thereby, the culture object 12 is not exposed to a flow in the vicinity of a rapid contractive flow. It is also possible to prevent the outflow of the culture object 12.

(8) By adjusting the flow rate, it is possible to select a flow such as an optimum laminar flow.

Second Embodiment

Figure 20:
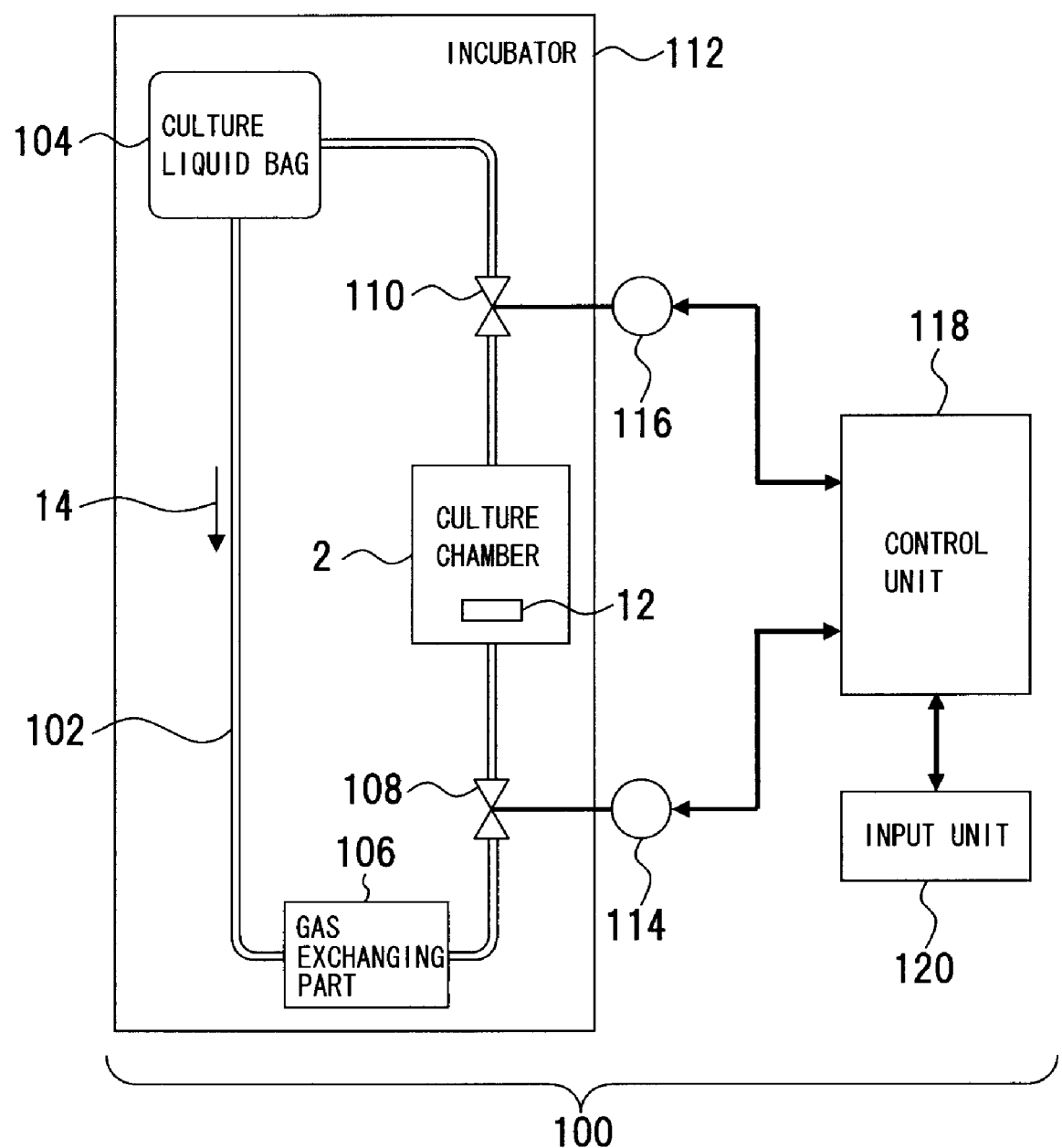
FIG. 20 is a drawing which shows a culture apparatus according to a second embodiment.

Next, a second embodiment of the present invention is explained by referring to FIG. 20. FIG. 20 is a drawing which shows a culture apparatus. In FIG. 20, the same portions as those of FIG. 1 and FIG. 11 are indicated by the same reference numerals.

This culture apparatus 100 is a constitution that cultivates the culture object 12 by using the culture chamber 2 described previously. The culture chamber 2 is integrated into a culture circuit 102. In this culture circuit 102, the circulating pipe 34 mentioned previously is used, and a culture liquid bag 104, a gas exchanging part 106, a perfusion pump 108 and a back pressure regulating valve 110 are also provided. This culture circuit 102 is built in an incubator 112. In the culture liquid bag 104, the culture liquid 14 including a nutrient necessary for cultivation, a growth factor and an antibiotic is stored. The gas exchanging part 106 is a gas permeating function part formed in the circulating pipe 34, and performs a gas exchange between an internal space of the incubator 112 and the culture liquid 14.

The perfusion pump 108 is a liquid supplying means which makes the culture liquid 14 circulate continuously or intermittently, and has an actuator 114, which generates driving power by an electric signal, at the exterior of the incubator 112. Further, the back pressure regulating valve 110 is a means which adjusts the back pressure of the culture chamber 2 correspondingly to the supply of the culture liquid 14, and has an actuator 116, which generates driving power by an electric signal, at the exterior of the incubator 112. To these actuators 114 and 116, a control unit 118 is connected. This control unit 118 is constituted by a personal computer and so on, and has a CPU (Central Processing Unit), and a ROM (Read-Only Memory) and a RAM (Random-Access Memory) as a storage means. In the ROM, a culture control program is stored. A desired control pattern is given to the actuators 114 and 116 from the control unit 118 by means of a set input which is input to an input unit 120, and a circulating form of the culture liquid 14 is controlled. For example, a flow rate, a back pressure regulating value and so on in relation to the culture liquid 14 are selected by the input unit 120, and a culture operation is executed by the control unit 118 in accordance with its instructions.

In a constitution like this, the culture liquid 14 flows through the culture circuit 102 by driving the perfusion pump 108. By the absorption of gas being performed at the gas exchanging part 106, the culture liquid 14 comes into a gas partial pressure almost equivalent to the gas partial pressure of the interior of the incubator 112. That is, the culture liquid 14 is adjusted to the culture liquid 14 which includes oxygen gas and carbon dioxide gas necessary for the cultivation. This culture liquid 14 is supplied to the culture chamber 2 by the perfusion pump 108, and cells or tissues which are culture object 12 are cultivated. The nutrient, the oxygen gas and so on are consumed from the culture liquid 14 by the culture object 12, and an exudation which exudes from the culture object 12 mixes into the culture liquid 14. The culture liquid 14 of the culture chamber 2 at its pressure is regulated by the back pressure regulating valve 110 and comes to the culture liquid bag 104.

In the culture apparatus 100 mentioned above, by installing the culture chamber 2 described previously, the culture liquid 14 which is supplied from the culture liquid bag 104 flows along the inner wall surfaces in the culture chamber 2 by the Coanda effect, and is diffused to be quickly exchanged. Along with this, there is nothing to give excessive stimulation and/or stress to the culture object 12 at the time of its exchange. Because of this, the culture apparatus 100 makes a contribution to the formation of an optimum culture environment.

In connection with the circulation of the culture liquid 14, there is a method in which the culture liquid 14 in the culture chamber 2 is gradually exchanged by feeding continuously the culture liquid 14, which is new, into the culture chamber 2 little by little by the drive of the perfusion pump 108. Further, there is a method in which the culture liquid 14 is exchanged by feeding the culture liquid 14 in a lump (however, without feeding rapidly) with a settled time interval by the drive of the perfusion pump 108. Either one of these methods may also be used, or these methods may also be combined. In addition, the culture liquid 14 which is fresh may also be always supplied to the culture chamber 2 by discharging the culture liquid 14, which is spent, into a bag different from the culture liquid bag 104 after passing the back pressure regulating valve.

Third Embodiment

Figure 21:
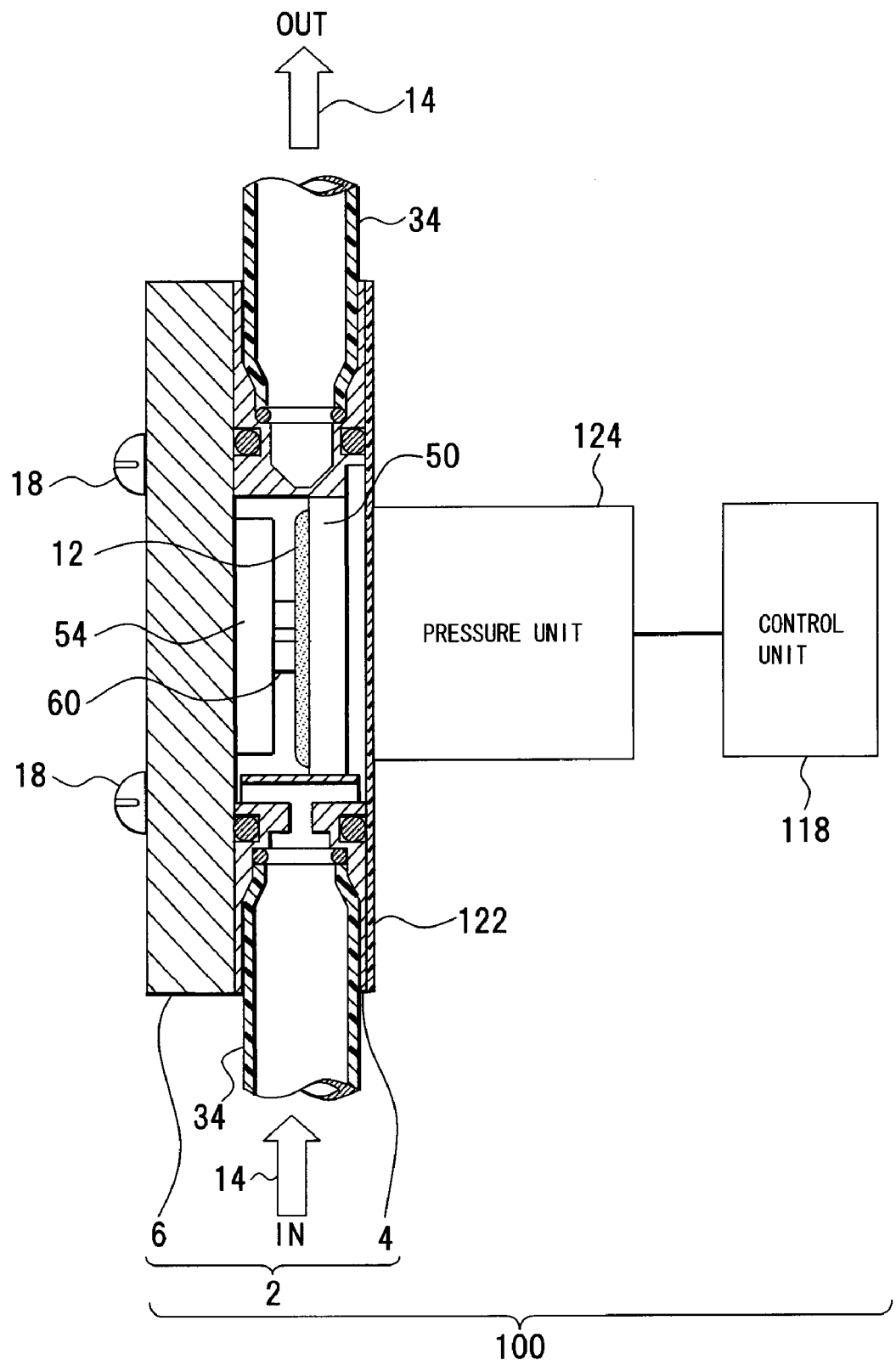
FIG. 21 is a drawing which shows a culture chamber according to a third embodiment.
Figure 22:
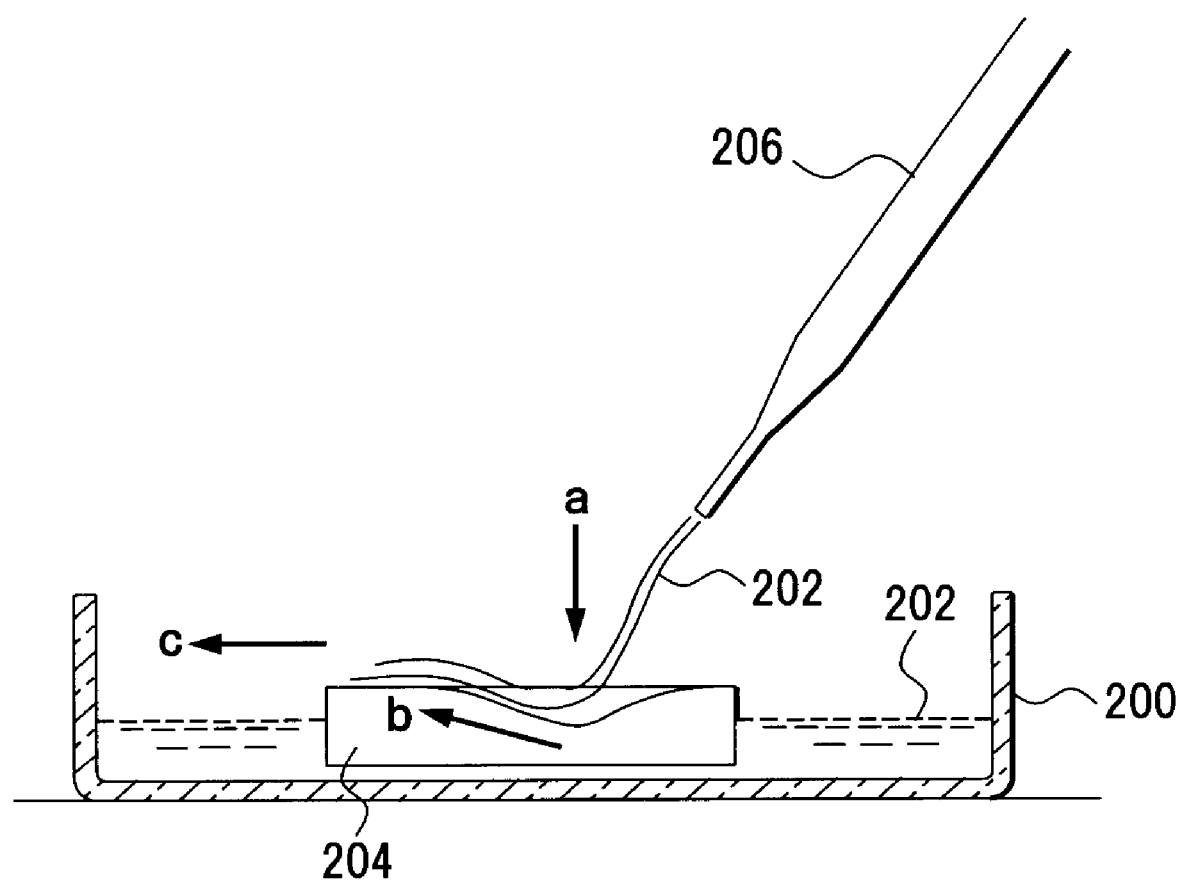
FIG. 22 is a drawing which shows a conventional exchange of a culture liquid.
Figure 23:
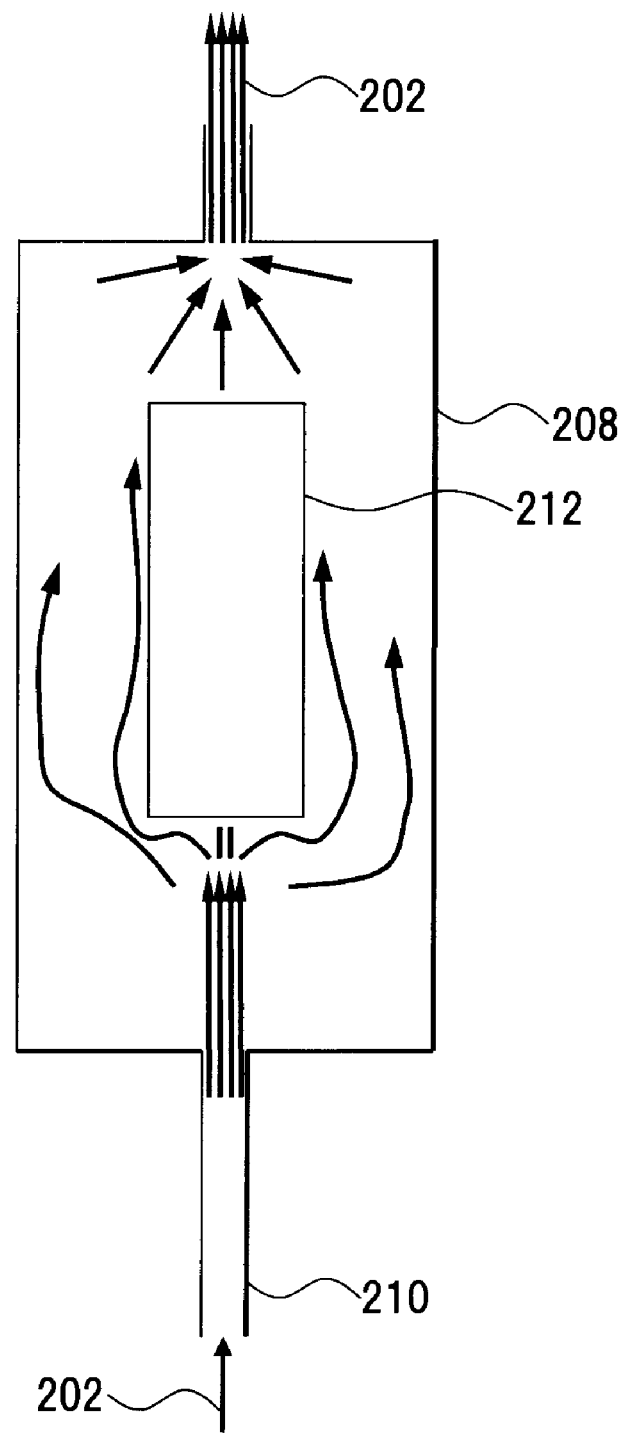
FIG. 23 is a drawing which shows a conventional exchange of a culture liquid.

Next, a third embodiment of the present invention is explained by referring to FIG. 21. FIG. 21 is a drawing which shows a culture chamber according to the third embodiment. In FIG. 21, the same portions as those of FIG. 111 are indicated by the same reference numerals.

To this culture chamber 2, instead of the blockading plate 8 mentioned previously, a pressure receiving plate 122 is provided. The culture chamber 2 is a constitution which gives a pressure force from an outside to the culture object 12 through the pressure receiving plate 122. The pressure receiving plate 122 can be formed by a PFA (tetrafluoroethylene perfluoroalkyl vinyl ether) film, for example. Further, a pressure unit 124 is provided to the pressure receiving plate 122, and culture chamber 2 is constituted so that the pressure unit 124 is controlled by the control unit 118 mentioned previously. According to a constitution like this, it is possible to give desired stimulation to the culture object 12 by the pressure force from the pressure unit 124.

As described above, the present invention relates to the culture chamber using the culture liquid, and its exchange function is heightened. Along with this, there is nothing to cause excessive stimulation and/or stress to the culture object. Therefore, the present invention can be widely utilized for the cultivation of cells or tissues of a human being or an animal.

Although the best mode for carrying out the invention, the object, the configuration and the operation and effect have been described in detail above, the invention is not limited to such embodiment for carrying out the invention, and it is a matter of course that the invention can be variously changed or modified by a person skilled in the art on the basis of a gist and split of the invention as disclosed in claims and the detailed description of the invention, and such a change or modification, and various conjectured configurations, modified examples and so forth are included in the scope of the invention, and the description of the specification and drawings are not restrictively understood.

What is claimed as new and desired to be protected by Letters Patent of the United States is:

1. A culture chamber which cultivates a culture object by circulating a culture liquid, comprising:
    a main body part;
    a culture space part that is formed in said main body part, houses said culture object, and circulates said culture liquid;
    blockading plates that are detachably attached to said main body part, and open and close said culture space part;
    an introducing part that is opened in a wall part of said main body part, and introduces said culture liquid into said culture space part;
    a discharging part that is opened in said wall part of said main body part, and discharges said culture liquid from said culture space part; and
    a flow arrangement part that is placed in said culture space part, said flow arrangement part causing said culture liquid, which is introduced into said culture space part from said introducing part, to diffuse from inner wall surfaces of said culture space part toward a direction which intersects a virtual line connecting said introducing part with said discharging part,
    wherein said culture space part includes a first inner wall surface that is formed in said main body part and surrounds said culture object, and second inner wall surfaces that are formed by said blockading plates and constitute said flow arrangement part,
    wherein said flow arrangement part includes:
    a vertical wall that has a wall surface opposite to a flow of said culture liquid introduced into said culture space part from said introducing part, and reduces flow velocity of said culture liquid;
    a small space part, at a side of said introducing part, that is surrounded by said vertical wall of said culture space part and an inner wall surface of said culture space part, said small space part being divided in said culture space part; and
    slit portions that are formed by said vertical wall and said second inner wall surfaces, and introduce said culture liquid, which is introduced into said small space part at the side of said introducing part, into said culture space part,
    wherein laminar flows along said second inner wall surfaces of said culture space part, respectively, are generated by said culture liquid passing through said slit portions from said small space part at the side of said introducing part, to diffuse said culture liquid from said laminar flows along said second inner wall surfaces, respectively, in said culture space part.

2. The culture chamber of claim 1 having a discharge flow-arrangement part that is formed in a side of said discharging part of said culture space part, said discharge flow-arrangement part guiding said culture liquid, which is led from the first inner wall surface, to said discharging part.

3. The culture chamber of claim 1, wherein said first inner wall surface forms a curved surface and said second inner wall surfaces form flat surfaces and are formed in a direction which intersects said first inner wall surface.

4. The culture chamber of claim 1 having a supporting part which bridges to a side of said discharging part from said flow arrangement part.

5. The culture chamber of claim 1, wherein said introducing part at a diameter of a passage passing said culture liquid is set smaller than said discharging part.

6. The culture chamber of claim 1, wherein protruding portions are provided at a midway part of said first inner wall surface.

7. A culture apparatus which cultivates a culture object by circulating a culture liquid, said culture apparatus including a culture chamber cultivating said culture object by circulating said culture liquid, said culture chamber comprising:
   a main body part;
   a culture space part that is formed in said main body part, houses said culture object, and circulates said culture liquid;
   blockading plates that are detachably attached to said main body part, and open and close said culture space part;
   an introducing part that is opened in a wall part of said main body part, and introduces said culture liquid into said culture space part;
   a discharging part that is opened in said wall part of said main body part, and discharges said culture liquid from said culture space part; and
   a flow arrangement part that is placed in said culture space part, said flow arrangement part causing said culture liquid, which is introduced into said culture space part from said introducing part, to diffuse from inner wall surfaces of said culture space part toward a direction which intersects a virtual line connecting said introducing part with said discharging part,
   wherein said culture space part includes a first inner wall surface that is formed in said main body part and surrounds said culture object, and second inner wall surfaces that are formed by said blockading plates and constitute said flow arrangement part,
   wherein said flow arrangement part includes:
   a vertical wall that has a wall surface opposite to a flow of said culture liquid introduced into said culture space part from said introducing part, and reduces flow velocity of said culture liquid;
   a small space part, at a side of said introducing part, that is surrounded by said vertical wall of said culture space part and an inner wall surface of said culture space part, said small space part being divided in said culture space part; and
   slit portions that are formed by said vertical wall and said second inner wall surfaces, and introduce said culture liquid, which is introduced into said small space part at the side of said introducing part, into said culture space part,
   wherein laminar flows along said second inner wall surfaces of said culture space part, respectively, are generated by said culture liquid passing through said slit portions from said small space part at the side of said introducing part, to diffuse said culture liquid from said laminar flows along said second inner wall surfaces, respectively, in said culture space part.

8. The culture apparatus of claim 7, wherein said culture chamber has a discharge flow-arrangement part that is formed in a side of said discharging part of said culture space part, said discharge flow-arrangement part guiding said culture liquid, which is led from the first inner wall surface, to said discharging part.

9. The culture apparatus of claim 7, wherein said first inner wall surface forms a curved surface and said second inner wall surfaces form flat surfaces and are formed in a direction which intersects said first inner wall surface.

10. The culture apparatus of claim 7, wherein said culture chamber has a supporting part which bridges to a side of said discharging part from said flow arrangement part.

11. The culture apparatus of claim 7, wherein said introducing part at a diameter of a passage passing said culture liquid is set smaller than said discharging part.

12. The culture apparatus of claim 9, wherein said culture chamber has protruding portions that are provided at a midway part of said first inner wall surface.

13. A liquid supplying method of a culture chamber which cultivates a culture object by circulating a culture liquid, comprising:
   housing said culture object in a culture space part of a main body part, attaching blockading plates that open and close said culture space part to said main body part, and introducing said culture liquid into said culture space part from an introducing part of said main body part;
   by a flow arrangement part in said culture space part, causing said culture liquid, which is introduced into said culture space part from said introducing part, to diffuse from inner wall surfaces of said culture space part toward a direction which intersects a virtual line connecting said introducing part with a discharging part;
   flowing said culture liquid which is caused to diffuse to said discharging part in said main body part; and
   discharging said culture liquid from said discharging part,
   wherein said culture space part includes a first inner wall surface that is formed in said main body part and surrounds said culture object, and second inner wall surfaces that are formed by said blockading plates and constitute said flow arrangement part,
   wherein in said flow arrangement part, said culture liquid is introduced into a small space part at a side of said introducing part, said small space part being divided in said culture space part by being surrounded by an inner wall surface of said culture space part and a vertical wall that has a wall surface opposite to a flow of said culture liquid introduced into said culture space part from said introducing part to reduce flow velocity of said culture liquid, and
   said culture liquid is introduced into said culture space part from said small space part at the side of said introducing part by passing through slit portions that are formed by said vertical wall and said second inner wall surfaces in a direction along said second inner wall surfaces, respectively, and
   wherein laminar flows along said second inner wall surfaces, respectively, are generated by said culture liquid introduced into said culture space part, to diffuse said culture liquid from said laminar flows along said second inner wall surfaces, respectively, in said culture space part.

14. A culture chamber which cultivates a culture object by circulating a culture liquid, comprising:
   a main body part;
   a culture space part that is formed in said main body part, houses said culture object, and circulates said culture liquid;
   blockading plates that are detachably attached to said main body part, and open and close said culture space part;
   an introducing part that is opened in a wall part of said main body part, and introduces said culture liquid into said culture space part;
   a discharging part that is opened in said wall part of said main body part, and discharges said culture liquid from said culture space part; and
   a flow arrangement part that is placed in said culture space part, said flow arrangement part causing said culture liquid, which is introduced into said culture space part from said introducing part, to diffuse from inner wall surfaces of said culture space part toward a direction which intersects a virtual line connecting said introducing part with said discharging part, wherein said culture space part includes a first inner wall surface that is formed in said main body part and surrounds said culture object, and second inner wall surfaces that are formed by said blockading plates and constitute said flow arrangement part, wherein said flow arrangement part includes:

a vertical wall that has a wall surface opposite to a flow of said culture liquid introduced into said culture space part from said introducing part, and reduces flow velocity of said culture liquid;

a small space part that, at a side of said introducing part, that is surrounded by said vertical wall of said culture space part and an inner wall surface of said culture space part, said small space part being divided in said culture space part; and slit portions that are formed by said vertical wall and said second inner wall surfaces, and introduce said culture liquid, which is introduced into said small space part at the side of said introducing part, into said culture space part, wherein, according to a flow rate of said culture liquid introduced through said slit portions from said small space part at the side of said introducing part, laminar flows along said second inner wall surfaces are generated, respectively, or said culture liquid spreads from said slit portions to lose said flow velocity, and if said culture liquid spreads from said slit portions to lose said flow velocity, accumulates a newly introduced culture liquid at a bottom part of said culture space part, and discharges said culture liquid at a top part of said culture space part by introducing said newly introduced culture liquid.

15. A culture apparatus which cultivates a culture object by circulating a culture liquid, said culture apparatus including a culture chamber cultivating said culture object by circulating said culture liquid, said culture chamber comprising:

a main body part;

a culture space part that is formed in said main body part, houses said culture object, and circulates said culture liquid;

blockading plates that are detachably attached to said main body part, and open and close said culture space part;

an introducing part that is opened in a wall part of said main body part, and introduces said culture liquid into said culture space part;

a discharging part that is opened in said wall part of said main body part, and discharges said culture liquid from said culture space part; and a flow arrangement part that is placed in said culture space part, said flow arrangement part causing said culture liquid, which is introduced into said culture space part from said introducing part, to diffuse from inner wall surfaces of said culture space part toward a direction which intersects a virtual line connecting said introducing part with said discharging part, wherein said culture space part includes a first inner wall surface that is formed in said main body part and surrounds said culture object and second inner wall surfaces that are formed by said blockading plates and constitute said flow arrangement part, wherein said flow arrangement part includes:

a vertical wall that has a wall surface opposite to a flow of said culture liquid introduced into said culture space part from said introducing part, and reduces flow velocity of said culture liquid;

a small space part that, at a side of said introducing part, that is surrounded by said vertical wall of said culture space part and an inner wall surface of said culture space part, said small space part being divided in said culture space part; and slit portions that are formed by said vertical wall and said second inner wall surfaces, and introduce said culture liquid, which is introduced into said small space part at the side of said introducing part, into said culture space part, wherein, according to a flow rate of said culture liquid introduced through said slit portions from said small space part at the side of said introducing part, laminar flows along said second inner wall surfaces are generated, respectively, or said culture liquid spreads from said slit portions to lose said flow velocity, and if said culture liquid spreads from said slit portions to lose said flow velocity, accumulates a newly introduced culture liquid at a bottom part of said culture space part, and discharges said culture liquid at a top part of said culture space part by introducing said newly introduced culture liquid.

16. A liquid supplying method of a culture chamber which cultivates a culture object by circulating a culture liquid, comprising:

housing said culture object in a culture space part of a main body part, attaching blockading plates that open and close said culture space part to said main body part, and introducing said culture liquid into said culture space part from an introducing part of said main body part;

by a flow arrangement part in said culture space part, causing said culture liquid, which is introduced into said culture space part from said introducing part, to diffuse from inner wall surfaces of said culture space part toward a direction which intersects a virtual line connecting said introducing part with a discharging part;

flowing said culture liquid which is caused to diffuse to a discharging part in said main body part; and discharging said culture liquid from said discharging part, wherein said culture space part includes a first inner wall surface that is formed in said main body part and surrounds said culture object, and second inner wall surfaces that are formed by said blockading plates and constitute said flow arrangement part, wherein in said flow arrangement part, said culture liquid is introduced into a small space part at a side of said introducing part, said small space part being divided in said culture space part by being surrounded by an inner wall surface of said culture space part and a vertical wall that has a wall surface opposite to a flow of said culture liquid introduced into said culture space part from said introducing part to reduce flow velocity of said culture liquid, and said culture liquid is introduced into said culture space part from said small space part at the side of said introducing part by passing through slit portions that are formed by said vertical wall and said second inner wall surfaces, and wherein, according to a flow rate of said culture liquid introduced to said culture space part, laminar flows along said second inner wall surfaces are generated, respectively, or said culture liquid spreads from said slit portions to lose said flow velocity, and if said culture liquid spreads from said slit portions to lose said flow velocity, a newly introduced culture liquid is accumulated at a bottom part of said culture space part, and said culture liquid at a top part of said culture space part is discharged by introducing said newly introduced culture liquid.

* * * * *